(12) United States Patent
Carn

(10) Patent No.: US 10,105,274 B2
(45) Date of Patent: Oct. 23, 2018

(54) ADJUSTABLE SURGICAL SUPPORT SYSTEM

(71) Applicant: Ronald M. Carn, Redding, CA (US)

(72) Inventor: Ronald M. Carn, Redding, CA (US)

( * ) Notice: Subject to any disclaimer, the term of this patent is extended or adjusted under 35 U.S.C. 154(b) by 309 days.

(21) Appl. No.: 15/040,914

(22) Filed: Feb. 10, 2016

(65) Prior Publication Data

US 2016/0228317 A1    Aug. 11, 2016

Related U.S. Application Data

(60) Provisional application No. 62/114,346, filed on Feb. 10, 2015.

(51) Int. Cl.
| | |
|---|---|
| *A61G 13/12* | (2006.01) |
| *A61G 13/00* | (2006.01) |
| *A61F 5/37* | (2006.01) |
| *A47C 20/00* | (2006.01) |
| *A61G 7/075* | (2006.01) |
| *A61G 13/10* | (2006.01) |

(52) U.S. Cl.
CPC .......... *A61G 13/125* (2013.01); *A47C 20/021* (2013.01); *A61F 5/37* (2013.01); *A61G 7/0755* (2013.01); *A61G 13/0036* (2013.01); *A61G 13/128* (2013.01); *A61G 13/1245* (2013.01); *A61G 13/1285* (2013.01); *A61G 13/101* (2013.01)

(58) Field of Classification Search
CPC .. A61G 13/12; A61G 13/1205; A61G 13/124; A61G 13/1245; A61G 13/125; A61G 13/126; A61G 13/128; A61G 13/1285; A61G 13/101; A61G 7/065; A61G 7/075; A61G 7/0755; A61G 7/0503; A61G 13/0036; A61G 13/0045; A61G 13/0063; A61F 5/37; A61F 5/3723; A61F 5/3769; A47C 20/021
See application file for complete search history.

(56) References Cited

U.S. PATENT DOCUMENTS

| | | | | |
|---|---|---|---|---|
| 3,020,909 | A | * | 2/1962 | Stevens .............. A61G 13/0036 5/623 |
| 3,240,516 | A | * | 3/1966 | Barish .................... A61G 13/12 248/284.1 |

(Continued)

*Primary Examiner* — Robert G Santos
*Assistant Examiner* — David R Hare
(74) *Attorney, Agent, or Firm* — Lowry Blixseth LLP; Scott M. Lowry

(57) ABSTRACT

The adjustable surgical support system includes a lower extremity support for receiving and supporting the foot and lower leg of a patient laying supine on an operating table. A ball mount extending downwardly from the lower extremity support is selectively insertable within one of a plurality of apertures arranged in a matrix and formed in an underlying base plate. The apertures are conical in nature such that the ball mount is stable to horizontal forces when placed therein. The base plate may include at least one upwardly open channel that receives a foot rest for anchoring the adjustable surgical support system to the operating table. Surgeons and other surgical personnel may adjust the position of the foot and/or lower leg during surgery by removing and selectively inserting the ball mount into any one of the other apertures in the base plate, or rotating the same within the selected aperture.

55 Claims, 15 Drawing Sheets

(56) References Cited

U.S. PATENT DOCUMENTS

| | | | | |
|---|---|---|---|---|
| 3,829,079 A * | 8/1974 | Fox | ............................ | A61H 1/00 128/870 |
| 4,717,133 A * | 1/1988 | Walsh | ...................... | A61G 13/12 188/290 |
| 4,807,864 A * | 2/1989 | Young | ...................... | A61G 13/12 403/143 |
| 5,390,383 A * | 2/1995 | Carn | ........................ | A61G 13/12 128/877 |
| 5,462,551 A * | 10/1995 | Bailey | ...................... | A61G 13/12 606/88 |
| 5,484,393 A * | 1/1996 | McCoy | ....................... | A61F 5/02 5/621 |
| 5,560,577 A * | 10/1996 | Keselman | ............... | A61F 5/3761 248/229.25 |
| 5,582,379 A * | 12/1996 | Keselman | ............... | A61F 5/3761 248/229.25 |
| 5,645,079 A * | 7/1997 | Zahiri | ..................... | A61F 5/3769 128/882 |
| 6,108,841 A * | 8/2000 | Cameron | ............ | A61G 13/0009 5/624 |
| 6,435,186 B1 * | 8/2002 | Klemm | .................. | A61B 90/60 128/845 |
| 6,629,944 B2 * | 10/2003 | Smart | ........................ | A61F 5/04 128/845 |
| 7,387,284 B2 * | 6/2008 | Chang | .................. | F16C 11/106 108/7 |
| 7,415,741 B1 * | 8/2008 | Wasley | ................... | A61G 13/12 5/621 |
| 7,832,035 B2 * | 11/2010 | Walczyk | ................ | A61G 13/12 5/623 |
| 7,836,890 B2 * | 11/2010 | Waterman | ............ | A61B 6/0421 108/1 |
| 8,028,702 B2 * | 10/2011 | DaSilva | ................ | A61G 13/12 128/845 |
| 8,099,808 B1 * | 1/2012 | McKeon | ............ | A61G 13/0063 5/621 |
| 8,302,228 B2 * | 11/2012 | Aboujaoude | ......... | A61F 5/3761 128/882 |
| 8,656,536 B1 * | 2/2014 | Sorg | ..................... | A61G 13/1205 378/209 |
| 8,782,832 B2 * | 7/2014 | Blyakher | .............. | A61B 6/0421 5/601 |
| 8,944,065 B2 * | 2/2015 | Slusarz, Jr. | .......... | A61B 5/0555 128/845 |
| 9,271,862 B2 * | 3/2016 | Hunter, Jr. | ............ | A61F 5/3761 |
| RE46,032 E * | 6/2016 | Torrie | .................. | A61H 1/0218 |
| 9,554,959 B2 * | 1/2017 | Carn | ..................... | A61G 13/123 |
| 2003/0167569 A1* | 9/2003 | Newkirk | ................ | A61G 13/12 5/613 |
| 2004/0123389 A1* | 7/2004 | Boucher | ................ | A61G 13/12 5/623 |
| 2007/0089239 A1* | 4/2007 | Whiteside | .............. | A61G 13/12 5/624 |

* cited by examiner

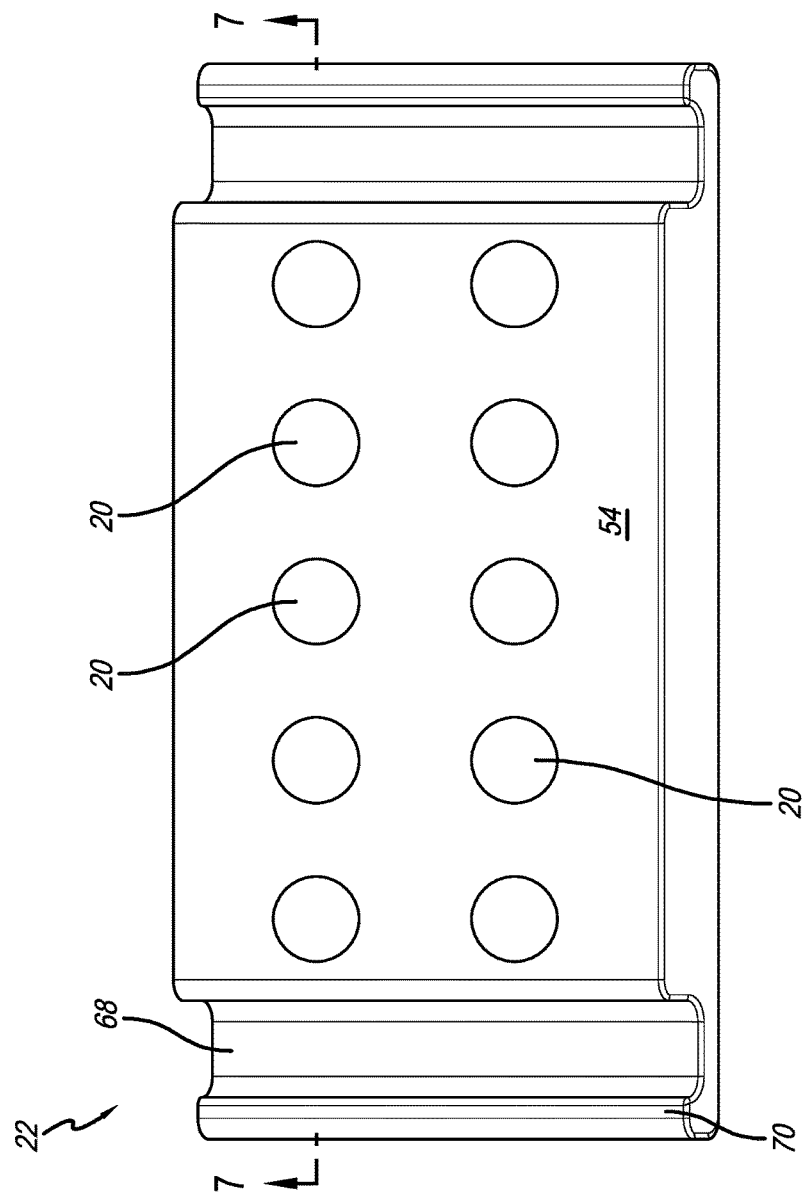

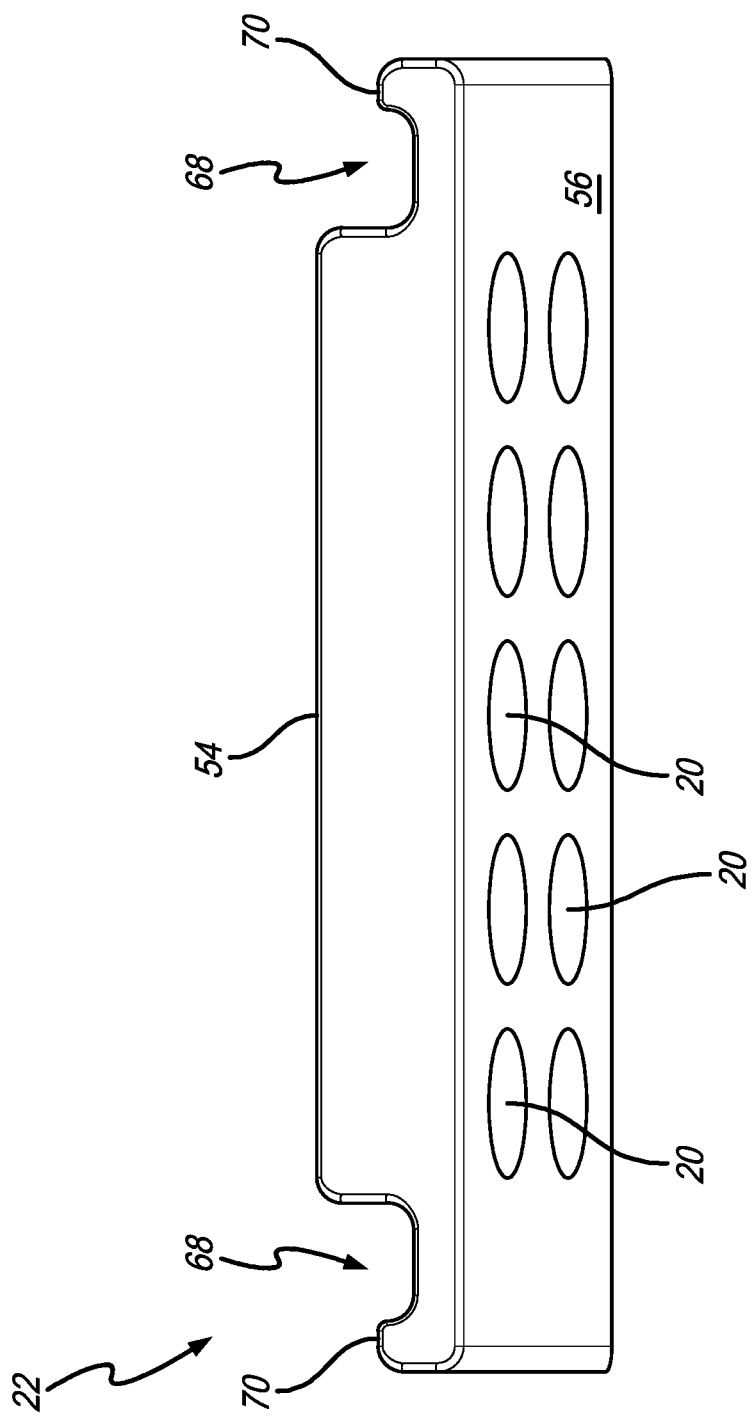

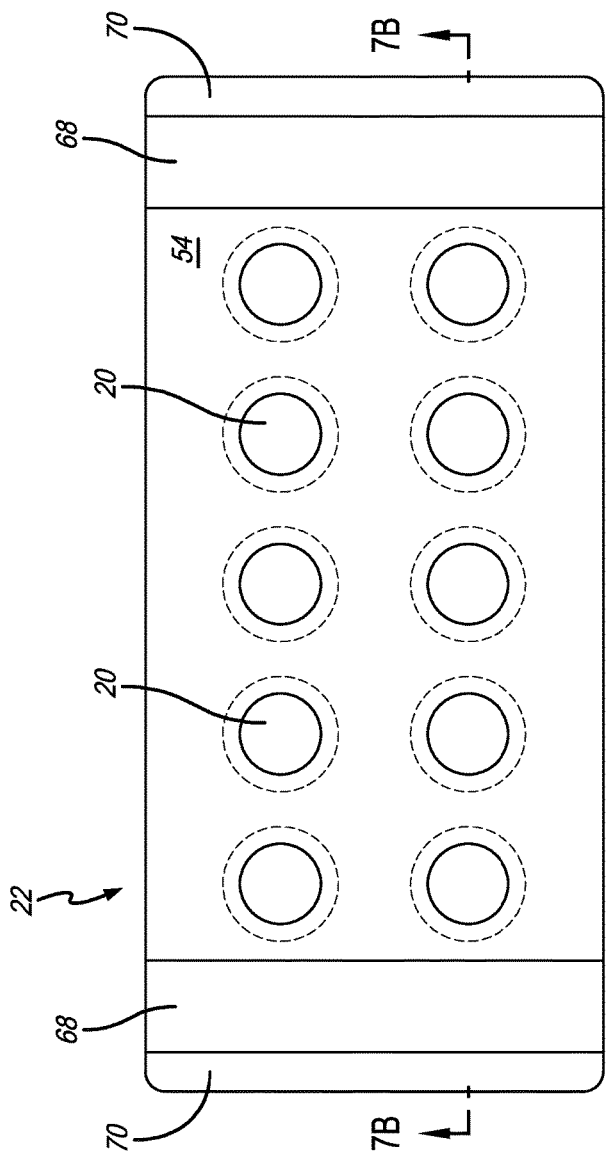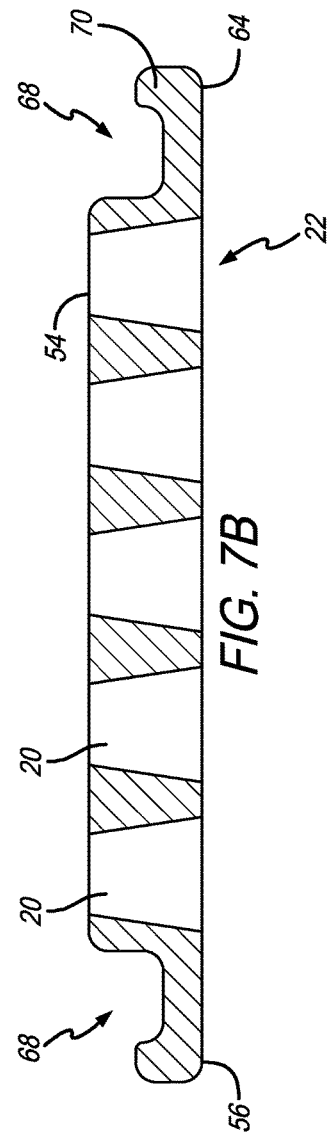

ADJUSTABLE SURGICAL SUPPORT SYSTEM

BACKGROUND OF THE INVENTION

The present invention is directed to an adjustable surgical support system for retaining and positioning the lower extremity of a patient during a surgical procedure. More specifically, the present invention relates to an adjustable surgical support system having a lower extremity support with a downwardly extending ball mount selectively insertable in and among one of a plurality of apertures formed in a base plate, for adjusting the position of the foot, lower leg and/or knee of a surgical patient laying in a supine position on an operating table during surgery (e.g., knee replacement).

Orthopedic surgery is the branch of surgery concerned with conditions involving the musculoskeletal system. Orthopaedic surgeons may use surgical, non-surgical or other minimally invasive procedures to treat musculoskeletal trauma, sports injuries, degenerative diseases, infections, tumors, etc. One particular area of orthopedic surgery concerns the knee joint, and includes surgical procedures such as total knee arthroscopy ("TKA"), partial knee arthroscopy, ligamentous reconstruction, cartilage reconstruction and fracture care. For example, the TKA procedure involves opening the knee (i.e., the surgical approach) and replacing worn out surfaces with new metal and/or plastic surfaces. Numerous devices such as mechanical instruments, computers and robots assist the surgeon in making the correct decisions and guiding the bone cuts. During these procedures (especially TKA), the knee must be securely positioned and supported in various orientations. Further to this point is that surgeons must move and reorient the knee into various positions of flexion during the surgery. This allows the surgeon to view different components of the knee and to ensure an optimum fit and function of the prosthesis.

A variety of support devices are known in the art for supporting the leg and foot while an anesthetized patient is laying in a supine position on an operating room table. These devices range from simple sand bags taped to the operating table to complex mechanical devices having multiple moving parts. The more complex support devices in particular permit positional adjustment of the foot, lower leg and/or knee during surgery. In this respect, these support devices are typically mounted via clamps or bars to a metal edge or rail of the operating table. Unfortunately, this creates an electrically conductive connection between the support device and the operating table. This can be particularly problematic when using electrocautery surgery devices. To mitigate the potential for current running through the patient during surgery, a ground is placed on the patient (e.g., on a gel pad). The problem occurs when current travels through the positioning device rather than the "ground" on the patient. This could result in electrical current passing through the patient, thereby causing burns or other injury. This is obviously highly undesirable, and could be avoided altogether if the positioning device does not form an electrically conductive connection to the operating table. Moreover, conventional adjustable support devices include moving parts that create needless wear and tear, complexity and pinch points. These devices can also undesirably constrain the rotation of the tibia relative to the femur.

For example, U.S. Pat. No. 8,302,228 to Aboujaoude discloses a lower extremity surgical positioning device that includes a foot assembly designed to support the lower leg and foot of a patient during surgery. More specifically, the Aboujaoude device includes the combination of an articulating and rotating frame or cradle that attaches to a foot assembly acting as a leg and foot splint firmly anchored or attached to the surgical table. The lower leg cradle securely attaches to the patient via a series of adjustable straps that wrap around the thigh, shin area, ankle, and foot of the patient. This is designed to prevent the extremity of the patient from moving independently of the cradle. The assembly securely affixes to a side rail on the operating table via a rail mounting clamp or rail mount. The rail mount connects to an operating table rail and is rotatable relative thereto. Once the extremity of the patient is securely attached to the lower leg cradle and foot assembly via the straps, the physician can manipulate the extremity. For example, Aboujaoude discloses a rack and gear configuration and multiple adjustable pivot points to lengthen and/or rotate various portions of the foot assembly, for purposes of aligning and/or compressing certain features of the foot, leg and/or knee, such as for setting a broken bone in the leg. The problem here is that the Aboujaoude positioning device includes several moving parts, which may create undesirable pinch points. Moreover, the direct attachment to the operating table (e.g., the rails) may allow for an electrically conductive connection between the patient and the operating table by virtue of being connected thereto. This is undesirable, as mentioned above.

The De Mayo Knee Positioner® sold by Imp® Innovative Medical Products, Inc. of 87 Spring Lane, Plainville, Conn. 06062 is a similar leg and knee positioning system that also includes a boot for receiving the lower leg and foot of the surgical patient. The system includes a base device having a rail that provides sliding guidance for a boot support coupled to a support clamp that selectively secures or otherwise attaches to the operating table through rotatable operation of a single lever clamp. The surgeon selectively controls flexion and extension of the knee by selectively unlocking and sliding the boot support in the rail along the length of the base. Like the Aboujaoude positioning device, the De Mayo Knee Positioner® includes pinch points within the rail and clamp areas and can create an electrically conductive connection between the patient and operating table potentially causing an undesirable "ground" for electrocautery or other electrical surgery devices. These features, as mentioned above, are highly undesirable.

Additionally, Innomed, Inc. of 103 Estus Drive, Savannah, Ga. 31404 manufactures and sells a series of knee and leg positioning products called the Robb Leg Positioner, Stulberg Leg Positioner and Stulberg Sliding Bolster, for use in knee surgeries. For instance, the Robb Leg Positioner includes a leg and foot support or cradle that includes a pair of outwardly projecting engagement cylinders that selectively rotatably engage one of a set of hooks formed from a base that sits or otherwise clamps to the operating table. A surgeon may flex or extend the knee during surgery by rotating the leg/foot support in a selected set of engaged hooks, or by selectively unhooking the engagement cylinders from one set of hooks and re-engaging the engagement cylinders in another set of hooks along the length of the base. The leg and foot support can pivot within the hooks around the central axis of the engagement cylinders. One drawback of the Robb Leg Positioner is that the exposed hooks are jagged and may undesirably snag gloves, clothing, or tools in the operating room. Furthermore, pinch points exist between the engagement cylinders and upstanding hooks, which could inadvertently slide out from engagement during a surgery. Additionally, the leg of the patient cannot be rotated and can only be located along a single plane, as opposed to laterally.

The Stulberg Leg Positioner is more closely related to the construction and operation of the Aboujaoude positioning device and the De Mayo Knee Positioner®, namely it is a leg and/or foot locking support mechanism that slides within a rail system integrated into a base, and can be locked thereto by a locking mechanism. Additionally, the Stulberg Sliding Bolster is basically a base plate attachable to an operating room table that includes a rail for providing sliding guidance of a foot bolster that can be locked relative thereto so the knee can be adjusted to different angles of knee flexion during surgery. These products include the same basic drawbacks discussed in more detail above related to moveable parts, pinch points and electrical conductivity between the patient and operating table.

The SPIDER2 Limb Positioner made by Smith & Nephew, Inc. of 150 Minuteman Road, Andover, Mass. 01810 is another leg positioning device known in the art that includes a plurality of movable joints or linkages that can be selectively engaged or disengaged through depression of a button or foot pedal. The SPIDER2 is complex, expensive and must remain powered at all times by a heavy battery pack attached at one end to operate. If the battery dies during surgery, this has obvious drawbacks since the device can no longer be repositioned during surgery. An electrically charged device can also be problematic in the event of a short or other electrical coupling of the device to the operating table and/or the patient.

There exist, therefore, a significant need in the art for an adjustable surgical support system that minimizes the number of moving components and otherwise eliminates any potential electrically conductive connection to the operating room table to prevent grounding of the device and conduction of electricity through the extremity of the patient resulting in burns, while permitting knee flexion and different amounts of medial or lateral movement of the foot relative to the hip. Such a system should include a lower extremity leg and/or foot support having a ball mount configured to be selectively received and/or repositioned within one of a plurality of conically shaped apertures in a base plate having a pair of channels at opposite ends thereof for selectively receiving a foot support attached to the operating table, thereby securing the base plate to the operating table while simultaneously electrically insulating the patient. The present invention fulfills these needs and provides other related advantages.

SUMMARY OF THE INVENTION

One embodiment of the adjustable surgical support system disclosed herein generally includes a lower extremity support for receiving and supporting a foot and lower leg of patient laying supine on an operating table. More specifically, the lower extremity support may include, in one embodiment, a foot plate for supporting the foot, a leg plate for supporting the lower leg, and a heel plate juxtaposed in between for supporting the heel. A ball mount extending downwardly and away from the heel plate may be selectively insertable and repositionable within one of a plurality of retention apertures arranged in a matrix in an underlying base plate. The apertures in the base plate are configured to stabilize the heel plate ball mount by way of having downwardly opening or enlarging sidewalls. In one embodiment, the apertures may conically open outwardly from a relatively narrow engagement opening at the top surface of the base plate to a relatively larger opening at or near the bottom of the base plate, such that the ball mount can be stabilized within the aperture with the weight of the supported extremity. The base plate ends preferably include an upwardly open channel offset from each edge of the base plate by an offset strip. The base plate end channels are of a size and shape to selectively receive a foot rest positioned under the surgical drapes and attachable to the operating table. In this respect, the adjustable surgical support system has no direct connection to the operating table and is, therefore, not electrically coupled thereto. Surgeons and other surgical personnel may adjust the position of the foot and/or lower leg, and consequentially the knee, by removing and reinserting the ball mount into different apertures in the base plate, and through rotation of the ball mount in any one of the apertures.

In another embodiment of the adjustable surgical support system disclosed herein, a base plate may include a plurality of retention apertures formed therein. A lower extremity support may include a heel plate positioned between a foot plate and a leg plate, the lower extremity support being configured to receive and retain a portion of the lower extremity. Moreover, a ball mount outwardly extending from the heel plate may be selectively insertable in rotatable relation in and among the plurality of retention apertures such that the lower extremity support is selectively removable from one of the plurality of retention apertures and selectively insertable within another of the plurality of retention apertures to vary knee flexion and to vary the lateral and medial position of a patient foot relative to a patient hip during surgery.

The heel plate may include a downwardly extending arcuate recess terminating below the foot plate and the leg plate such that a patient heel is supported by the foot plate and the leg plate in an elevated position above the arcuate recess. In one embodiment, the arcuate recess may have a 2-4 inch radius. The base plate may also include at least one channel having a size and shape to selectively receive a clamp therein. An offset strip upwardly extending from one side of the at least one channel may have a height relatively smaller than a height of the base plate where the retention apertures are formed therein, and be used to provide enhanced engagement with the clamp. Preferably, the clamp secures the base plate to an operating table in electrical isolation relative thereto.

Moreover, the ball mount may further include a connecting shaft having a diameter relatively larger than each of the plurality of retention apertures. The connecting shaft may taper into a shoulder terminating in a constant diameter extension shaft having a diameter relatively smaller than the connecting shaft. The extension shaft may then terminate in a relatively larger diameter spherical mount insertable within any of the plurality of retention apertures. In one embodiment, the connecting shaft may have a 1.0 to 2.0 inch diameter, the extension shaft may have a 0.3 to 0.9 inch diameter, and the spherical mount may have a 0.75 to 1.25 inch diameter. The shoulder preferably includes a width relatively larger than the plurality of retention apertures and contacts a top surface of the base plate in sliding relation relative thereto when the ball mount is selectively positioned within one of the plurality of retention apertures. The plurality of retention apertures may include an inverse conical shape whereby the retention apertures expand downwardly from a top surface of the base plate. In this embodiment, the ball mount may be of a size and shape to contact an interior surface sidewall of the inverse conical retention aperture to apply a tangential force there-against when inserted therein. Here, the interior surface sidewall of each of the inverse conical retention apertures may also include a plurality of concentric grooves for friction engagement with the ball mount when inserted therein.

In another embodiment, an adjustable surgical support system generally includes a base plate having a plurality of retention apertures formed therein and a lower extremity support configured to receive and retain a portion of the lower extremity of a patient. The lower extremity support may include a heel plate positioned between a foot plate and a leg plate, wherein the heel plate includes a downwardly extending arcuate recess terminating below the foot plate and the leg plate such that a patient heel is supported by the foot plate and the leg plate in an elevated position above the arcuate recess. Additionally, a ball mount outwardly extending from the heel plate includes a connecting shaft that tapers into a shoulder having a width relatively larger than each of the plurality of retention apertures and contacts a top surface of the base plate in sliding relation relative thereto when a relatively smaller diameter spherical mount extending therefrom is selectively positioned within one of the plurality of retention apertures. Here, the spherical mount is selectively insertable in rotatable relation in and among the plurality of retention apertures such that the lower extremity support is selectively removable from one of the plurality of retention apertures and selectively insertable within another of the plurality of retention apertures to vary knee flexion and to vary the lateral and medial position of a patient foot relative to a patient hip during surgery.

In one embodiment, the arcuate recess may be a 2-4 inch radius and the spherical mount may be selectively insertable in each of the plurality of retention apertures in 360 degree rotatable relation relative thereto. In another aspect of this embodiment, an extension shaft may be positioned between the shoulder and the spherical mount, wherein the connecting shaft has a 1.0 to 2.0 inch diameter, the extension shaft has a 0.3 to 0.9 inch diameter, and the spherical mount has a 0.75 to 1.25 inch diameter. Preferably, each of the plurality of retention apertures includes an inverse conical shape that expands downwardly from a top surface of the base plate. The spherical mount may include a size and shape to contact an interior surface sidewall of the inverse conical retention aperture having a plurality of concentric grooves formed therein to apply a tangential force there-against in friction relation. The base plate may also include at least one channel having a size and shape to selectively receive a clamp therein and an offset strip upwardly extending from one side thereof adjacent the at least one channel, the offset strip having a height relatively smaller than the top surface of the base plate, wherein the clamp secures the base plate to an operating table in electrical isolation relative thereto.

In another embodiment, the adjustable surgical support system may include a base plate having a plurality of retention apertures having an inverse conical shape expanding downwardly from a top surface of the base plate. The base plate may include at least one channel formed therein and have a size and shape to select reception of a clamp therein. An offset strip upwardly extending from one side of the at least one channel may have a height relatively smaller than a height of the top surface of the base plate. As such, the clamp may selectively engage the at least one channel over the offset strip to secure the base plate to an operating table in electrical isolation relative thereto.

In another aspect of this embodiment, a lower extremity support having a heel plate positioned between a foot plate and a leg plate may be configured to receive and retain a portion of the lower extremity. Here, the heel plate may include a downwardly extending arcuate recess terminating below the foot plate and the leg plate such that a patient heel is supported by the foot plate and the leg plate in an elevated position above the arcuate recess. The arcuate recess of the heel plate may include a 2-4 inch radius.

Furthermore, the adjustable surgical support system may include a ball mount outwardly extending from the heel plate and selectively insertable in rotatable relation in and among the plurality of retention apertures such that the lower extremity support is selectively removable from one of the plurality of retention apertures and selectively insertable within another of the plurality of retention apertures to vary knee flexion and to vary the lateral and medial position of a patient foot relative to a patient hip during surgery. Here, the ball mount may include a size and shape for contacting an interior surface sidewall of the inverse conical retention aperture to apply a tangential force there-against when inserted therein. In one embodiment, the interior surface sidewall of each of the inverse conical retention apertures may include a plurality of concentric grooves for friction engagement with the ball mount. The ball mount may also include a connecting shaft having a diameter relatively larger than each of the plurality of retention apertures. The connecting shaft may taper into a shoulder terminating in a constant diameter extension shaft having a diameter relatively smaller than the connecting shaft. The extension shaft then terminates in a relatively larger diameter spherical mount insertable within any of the plurality of retention apertures. Here, the shoulder may include a width relatively larger than the plurality of retention apertures and may contact the top surface of the base plate in sliding relation relative thereto when the ball mount is selectively positioned within one of the plurality of retention apertures. In one embodiment, the connecting shaft includes a 1.0 to 2.0 inch diameter, the extension shaft includes a 0.3 to 0.9 inch diameter, and the spherical mount includes a 0.75 to 1.25 inch diameter.

The steps for using the adjustable surgical support system may include a patient lying down on an operating table in a supine position and then having surgical personnel attach a foot rest and a thigh support to the operating table to stabilize the position of the patient. Surgical personnel may then cover the patient with surgical blankets (drapes). Next, the base plate may be placed on the operating table with one of the channels disposed under the foot rest, thereby securing the base plate to the operating table. The next step is to place the foot and the lower leg of the patient into the lower extremity support. The lower extremity support and the foot and lower leg are then wrapped with a sterile wrap to prevent relative movement therebetween. The ball mount is then placed into one of the plurality of apertures such that the foot and lower leg are securely positioned to facilitate knee surgery. Of course, the lower extremity support may be rotated within the aperture to obtain the optimal position for the procedure, and the ball mount may be removed and reinserted into a different aperture during surgery, so the surgeon can obtain the desired bending, flexion, medial and/or lateral position of the knee, in an efficient manner and without any moving parts or complex mechanisms.

In another method for securing and adjusting a lower extremity of a patient during surgery as disclosed herein, one step may include clamping a base plate having a plurality of retention apertures therein to an operating table in non-conductive relation relative thereto. Another step may include securing the lower extremity of the patient to a lower extremity support that includes a heel plate positioned between a foot plate and a leg plate, the heel plate having a downwardly extending arcuate recess terminating below the foot plate and the leg plate such that a patient heel is supported by the foot plate and the leg plate in an elevated position above the arcuate recess. A ball mount outwardly extending from the heel plate may be inserted, removed, and/or reinserted into or out from one of the retention apertures in the base plate during surgery. Furthermore, when in one of the plurality of retention apertures, the ball mount may be rotated therein. As such, removing, reinserting, and rotating of the ball mount varies knee flexion and the lateral and medial position of a patient foot relative to a patient hip during surgery.

In another aspect of this embodiment, the clamping step may include the step of securing a foot rest within a channel in the base plate and over an offset strip having a height relatively shorter than the height of the base plate. Here, the offset strip may help prevent the base plate from moving under the foot rest. Additionally, the combination of the lower extremity support and the lower extremity of the patient may be wrapped with a sterile wrap. The inserting and/or the reinserting steps may include the step of positioning the ball mount within one of the retention apertures that includes an inverse conical shape. Here, tilting the ball mount within the retention aperture may tangentially contact a sidewall of the inverse conical retention aperture. The inserting step may also include the step of placing a tapering shoulder having a width relatively larger than each of the plurality of retention apertures on a top surface of the base plate in sliding rotation relative thereto. Lastly, the inserting step may alternatively include the step of course positional adjustment and/or the rotating step may include the alternative step of fine positional adjustment.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 5 is a top view of the base plate, further illustrating a matrix of apertures formed therein and a pair of upwardly open channels at each end;

FIG. 6 is a side view of the base plate of FIG. 5, further illustrating the upwardly open channels;

FIG. 7A is a top view of the base plate having a two by five matrix of the conical apertures;

FIG. 7B is a cross-sectional view of the base plate taken generally about line 7-7 in FIG. 5, further illustrating one row of the conically shaped apertures;

DETAILED DESCRIPTION OF THE PREFERRED EMBODIMENTS

Figure 12:
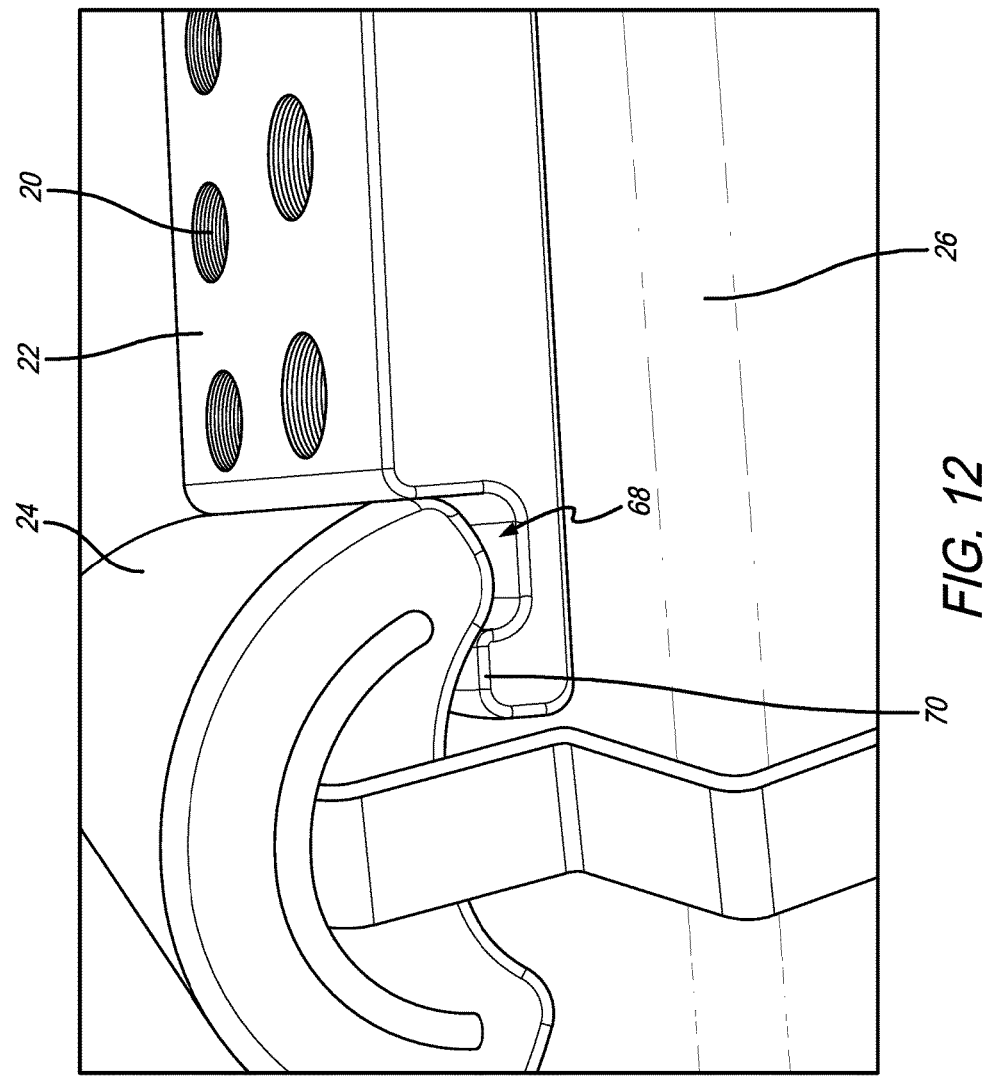
FIG. 12 is an enlarged side view of the base plate having a foot rest engaged with one of the channels.
Figure 13:
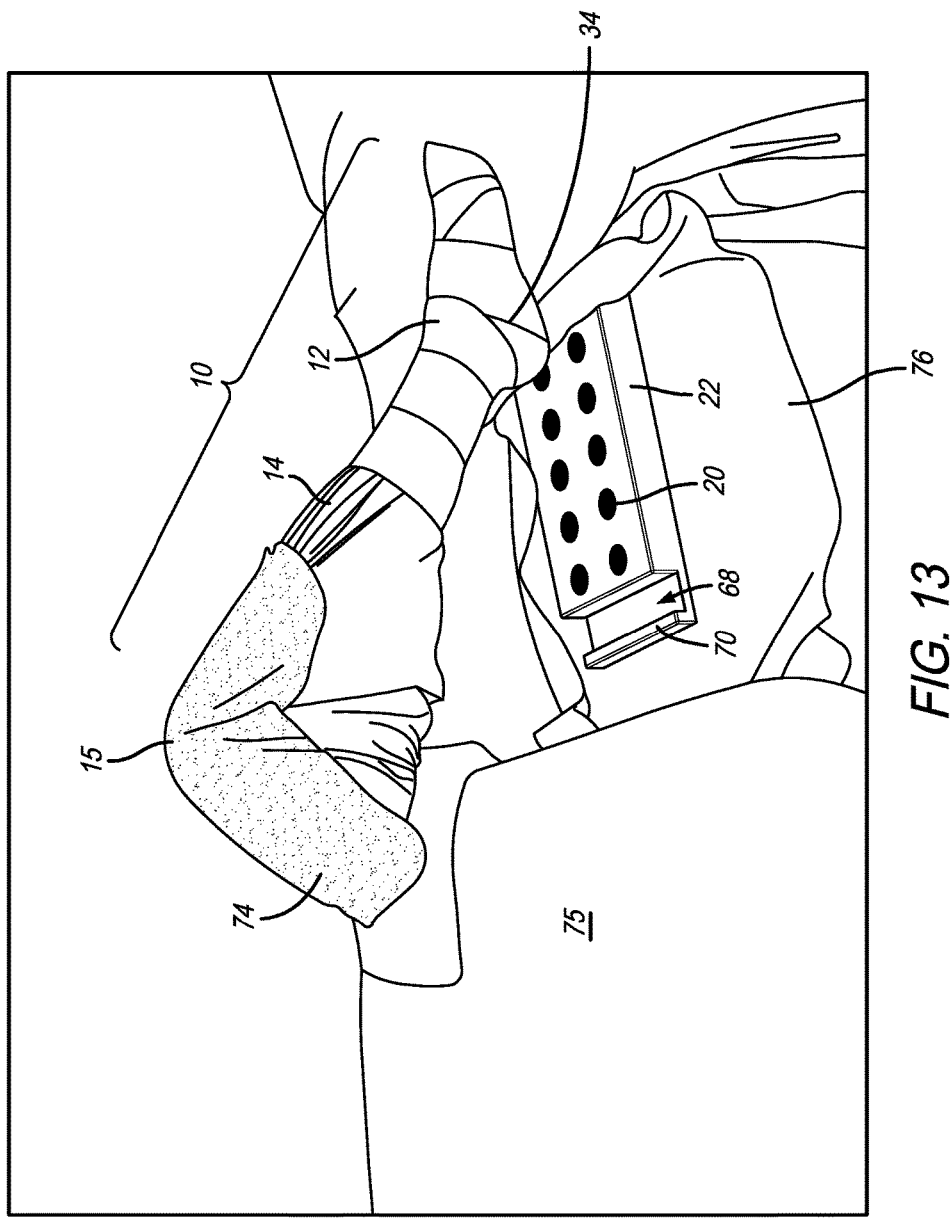
FIG. 13 is an environmental view illustrating the position of the lower leg and foot of a surgical patient relative to the base plate and the foot rest after insertion of the foot rest into one of the channels in the base plate.
Figure 14:
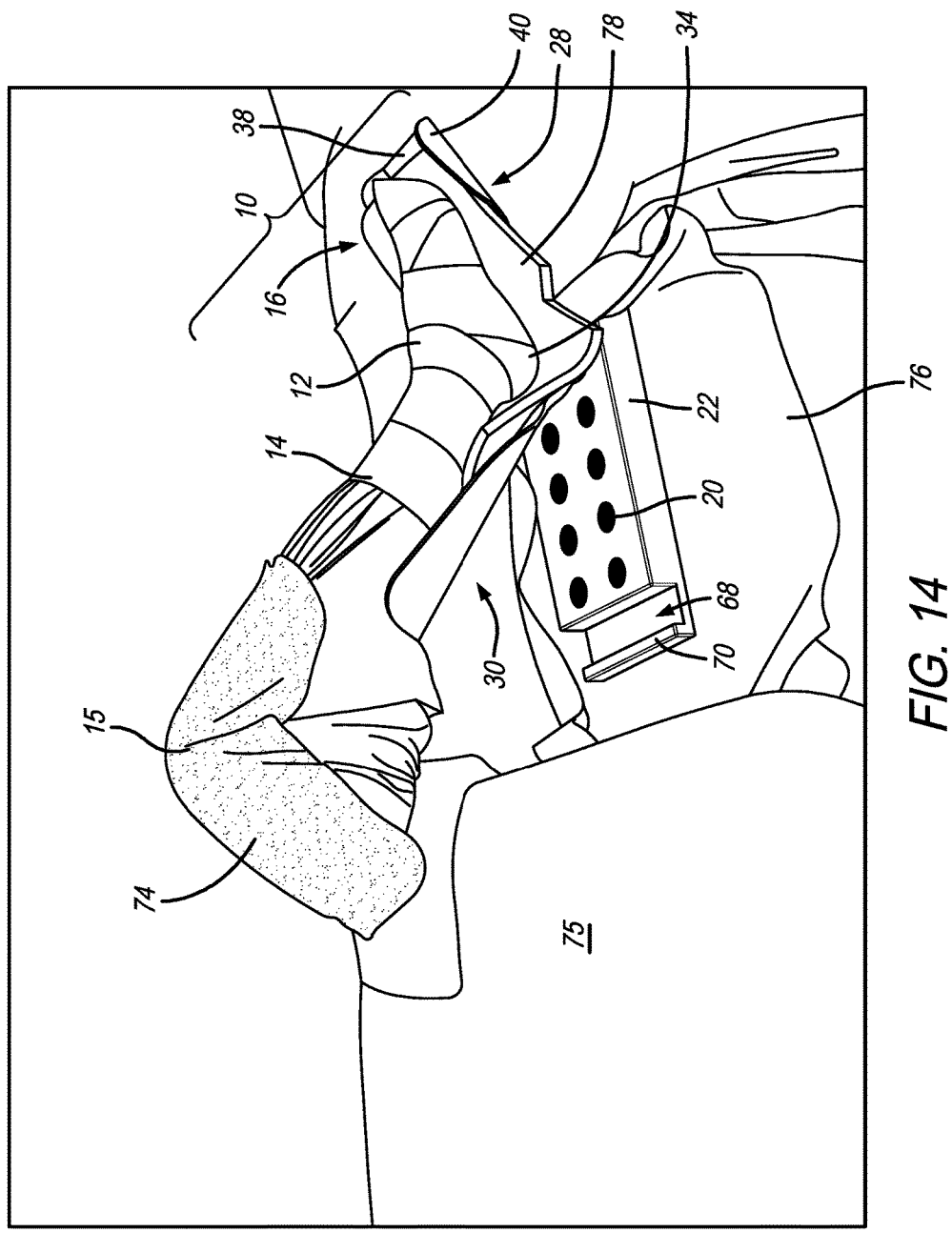
FIG. 14 is an environmental view similar to FIG. 13, further illustrating the lower leg and foot of the surgical patient resting on a foam pad lining the interior of the lower extremity support, with the ball mount of the support engaged with one of the conical apertures in the base plate.
Figure 15:
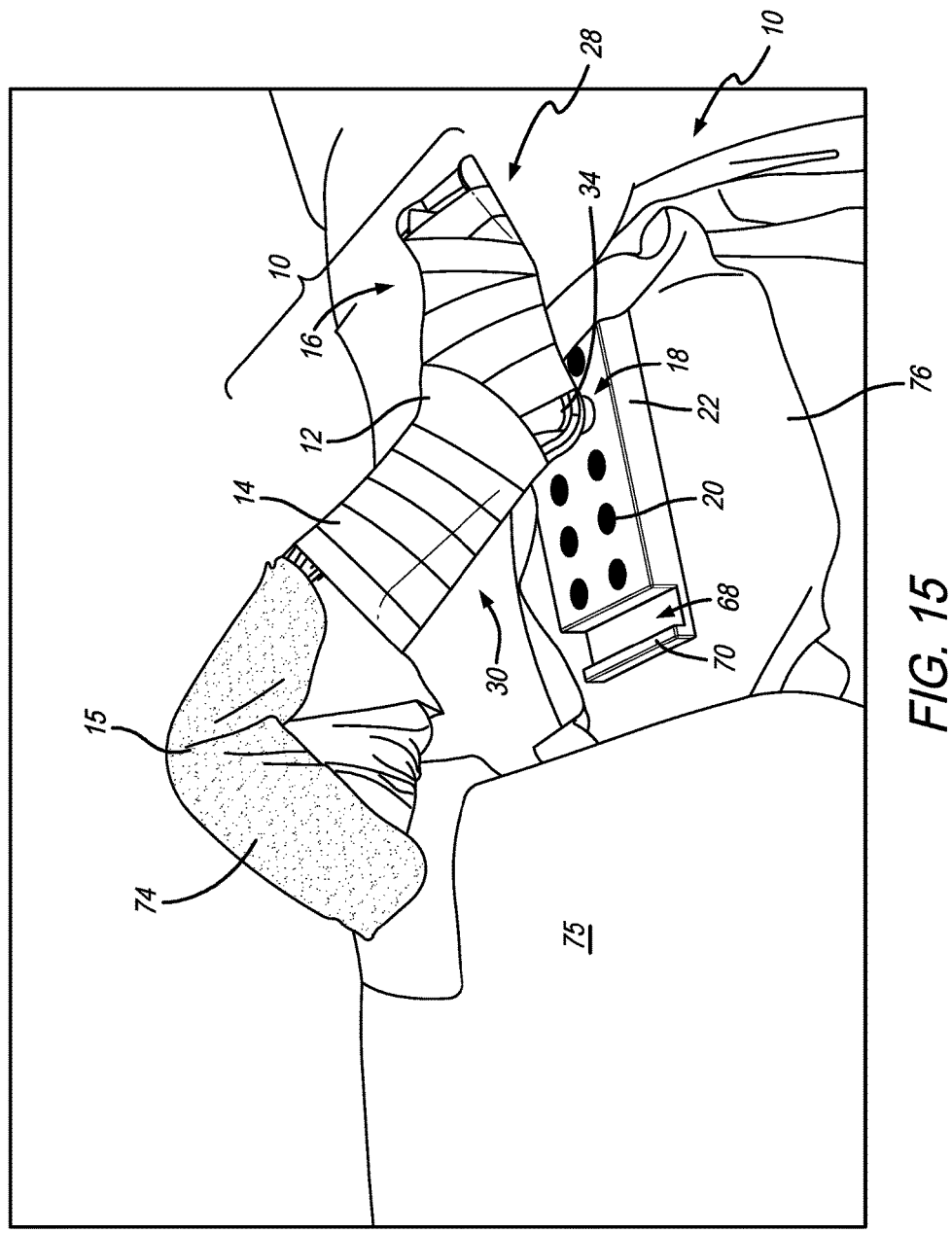
FIG. 15 is an environmental view similar to FIGS. 13 and 14, further illustrating the lower leg and foot of the surgical patient wrapped to the lower extremity support engaged with the base plate.

As shown in the drawings for the purposes of illustration, the present disclosure for an adjustable surgical support system is generally referred to by reference numeral 10 in FIGS. 1, 11 and 13-15. As illustrated in FIGS. 13-15, the adjustable surgical support system 10 generally supports a foot 12 and/or a lower leg 14 (e.g., ankle and calf area) to selectively position and/or relocate a knee 15 of a patient, in a position that facilitates various surgical procedures, such as TKA, ligamentous reconstruction and fracture care. In this respect, the support system 10 includes a lower extremity support 16 that receives and supports the foot 12 and/or the lower leg 14 as shown best in FIGS. 14-15. A ball mount 18 extends outwardly down and away from the lower extremity support 16 and is configured for selective slide-in engagement with one of a plurality of apertures 20 formed from a base plate 22, such as the two by five matrix of apertures shown, for example, in FIGS. 1, 5, 11-15. A foot rest 24 may be used to secure the base plate 22 to an operating table 26 in the manner generally shown in FIG. 1 and more specifically shown in FIG. 12. Advantageously, surgical personnel may quickly and easily adjust the position of the foot 12, the lower leg 14 and/or the knee 15 without using slides or clamps. For instance, the lower extremity support 16 is shown in FIG. 15 inserted into one of the apertures 20 (specifically row 2, column 2). Readjustment is only a matter of removing the ball mount 18 out from within the aperture 20 (row 2, column 2), relocating the ball mount 18 above another one of the apertures 20 to attain the desired flexion and rotation of the knee 15 (and possibly the foot 12 and/or the leg 14, as needed), and then re-inserting the ball mount 18 into the then underlying aperture 20. In this respect, the adjustable surgical support system 10 does not include any sliding components and otherwise does not form an electrical connection with the operating table 26 that could pose a danger to the patient.

Figure 1:
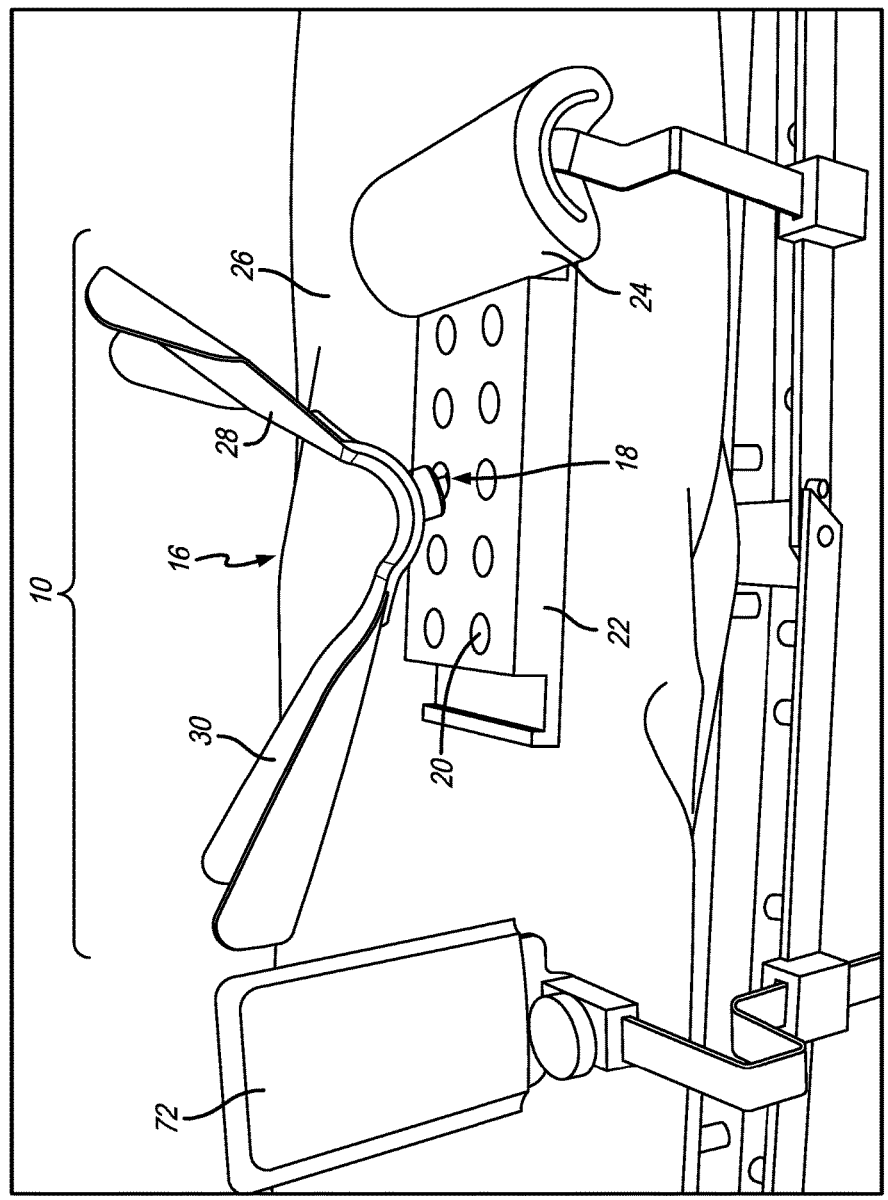
FIG. 1 is a perspective view illustrating the preferred components of an adjustable surgical support system as disclosed herein.
Figure 2A:
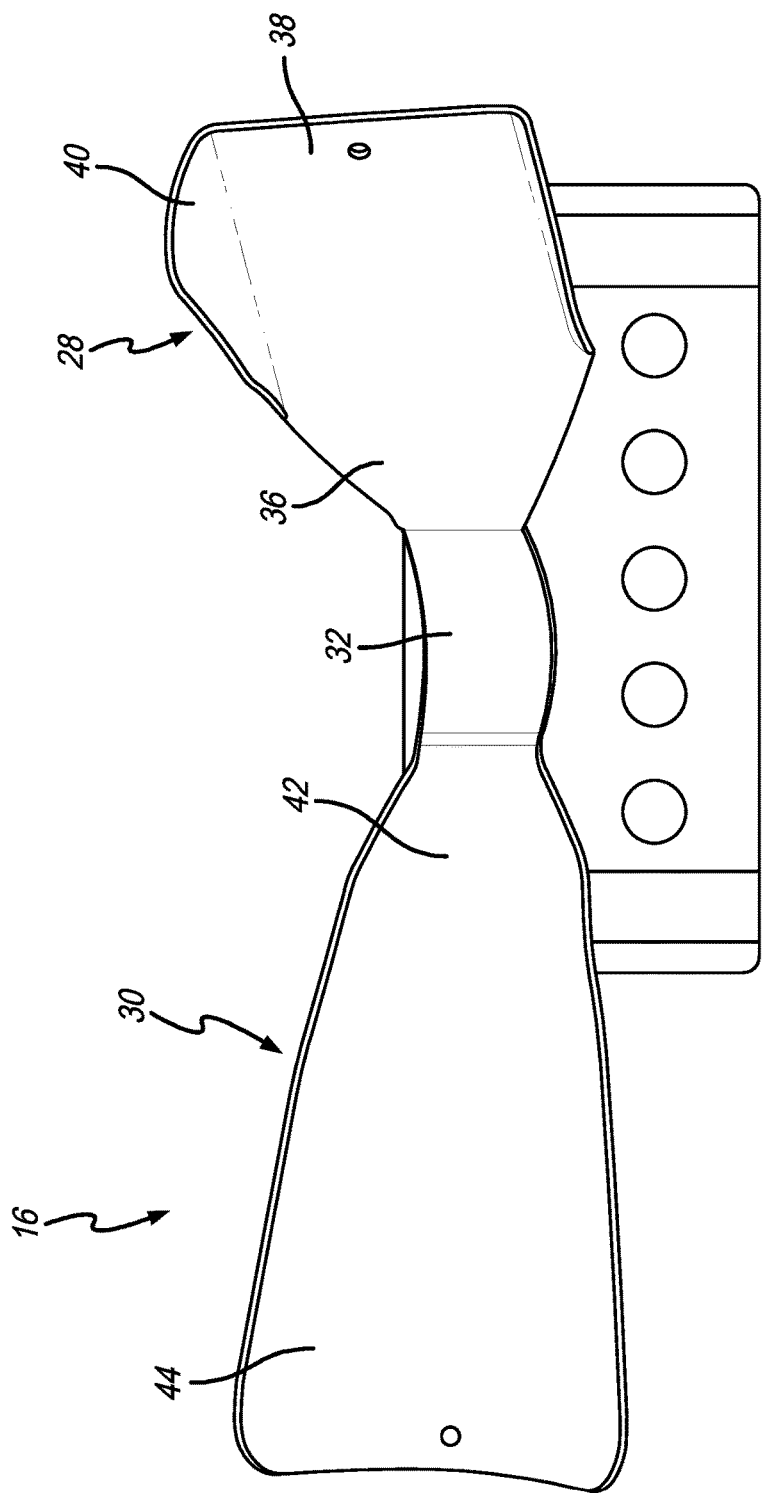
FIG. 2A is a top view more specifically illustrating a foot plate, a leg plate and a heel plate of a lower extremity support engaged with a base plate.
Figure 2C:
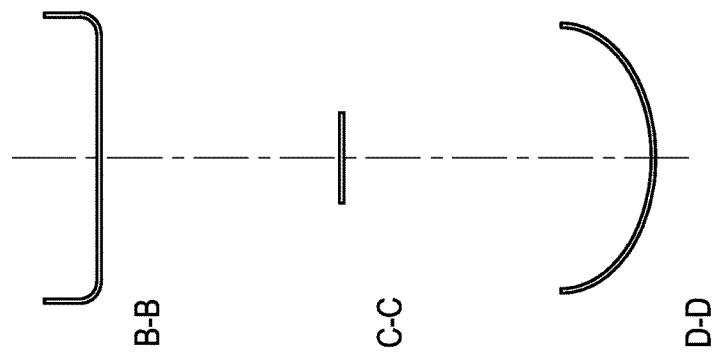
FIG. 2C is a cross-sectional view of the lower extremity support shown in FIG. 2B, illustrating the cross-section of the foot plate taken about the line B-B, the cross-section of the heel plate taken about the line C-C, and the cross-section of the leg plate taken about the line D-D in FIG. 2A.
Figure 2B:
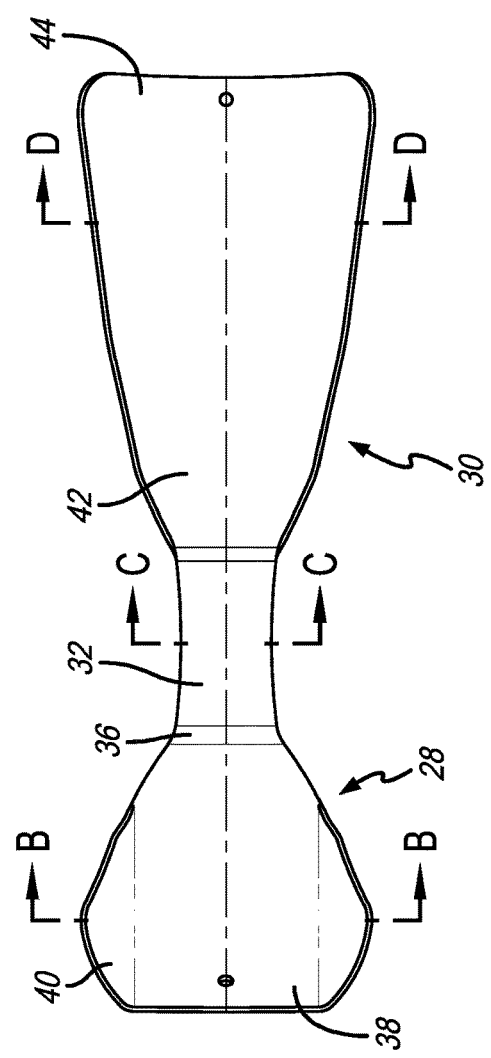
FIG. 2B is a top schematic view of the lower extremity support shown in FIG. 2A.
Figure 3:
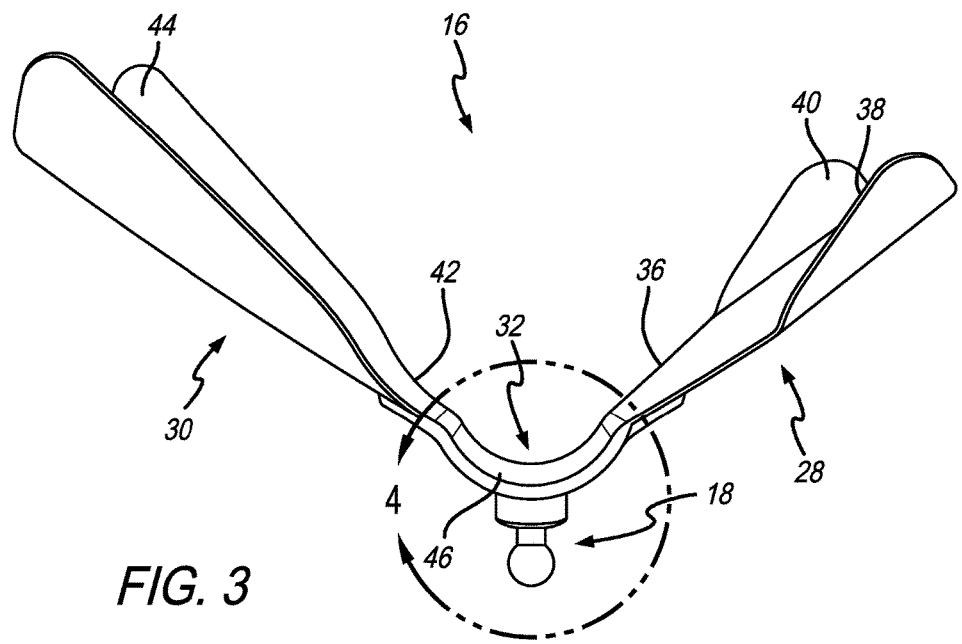
FIG. 3 is a perspective side view of the lower extremity support of FIG. 2A.

As illustrated best in FIGS. 1 and 3, the lower extremity support 16 is generally L-shaped and configured to support the leg, ankle and foot. More specifically, the lower extremity support 16 includes a foot plate 28 and a leg plate 30 for respectively supporting the foot 12 and the lower leg 14 of the patient, as shown best in FIGS. 14 and 15. A heel plate 32 is juxtaposed between the foot plate 28 and the leg plate 30 and is relatively narrow in width as shown in FIGS. 2A-2C. FIG. 3 illustrates that the heel plate 32 has a generally concave or arcuate shape to prevent localized pressure over a heel 34 of the patient. This allows the lower extremity support 16 to support the ankle in a neutral position, resulting in a more even distribution of forces such as with impacting knee replacement parts into the tibia bone as part of a knee replacement. The heel plate 32 may form a slightly obtuse angle (e.g., approximately between 100° and 120°) between the foot plate 28 and the leg plate 30. In this respect, the lower extremity support 16 prevents hyperextension of the ankle and toes as these body parts are contained in and supported by the support 16.

The foot plate 28 is a generally flat and plate-like member having a proximal end 36 coupled to the heel plate 32 and a distal end 38 having a pair of outwardly-extending or flaring side walls 40. These side walls 40 help prevent the foot 12 from slipping off the side of the foot plate 28. In the embodiment shown in FIGS. 2A-3, the side walls 40 are generally triangular in shape and start to extend upwardly and generally outwardly approximately halfway up the length of the foot plate 28, and increase in size toward the distal end 38 as shown. The side walls 40 are shown being approximately the same size and shape, but persons of ordinary skill in the art will recognize that other shapes, sizes and configurations may be utilized, depending on the need. For example, the pair of side walls 40 may alternatively be rectangular, hemispherical, etc. and may be sized for retaining different size feet. In a particularly preferred embodiment, the foot plate 28 is able to accommodate a size 12 foot (length) having a 5 inch width. Additionally, each side wall 40 may be a different size or shape, and the lower extremity support 16 may include both of the side walls 40 as shown, one side wall 40 or no side walls at all. In one embodiment, the distal end 38 of the foot plate 28 may be twice as wide as the proximal end 36 of the foot plate 28.

The leg plate 30 is a generally concave and upwardly extending partial hollow cylinder having a proximal end 42 coupled to the heel plate 32 and a distal end 44 flaring outwardly and having a size and shape to retain the lower leg 14 (e.g., the calf) of the surgical patient. In one embodiment, the leg plate 30 is approximately 14 inches long and 6 inches wide. The leg plate 30 is initially generally flat in about the proximal end 42 for providing a smooth transition to the heel plate 32. The leg plate 30 then flares upwardly and distally outwardly in a curved manner, as shown. Specifically with respect to FIGS. 1, 2A and 3, the distal end 44 has a generally parabolic shape designed to cup or hold the lower leg 14 to prevent it from sliding off the leg plate 30, and is preferably wide enough to accommodate the lower leg 14 when wrapped with a sterile dressing such as the Coban™ self-adherent wrap sold by 3M Company of St. Paul, Minn. 55144. Of course, the distal end 44 may be any suitable shape (e.g., rectangular) or size known in the art. In one embodiment, the distal end 44 of the leg plate 30 may be twice as wide as the proximal end 42 of the leg plate 30.

Figure 4:
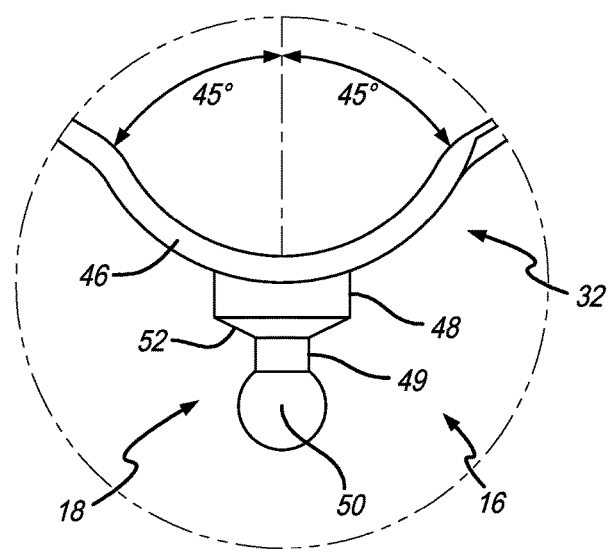
FIG. 4 is an enlarged perspective side view of the heel plate and a ball mount of the lower extremity support, taken about the circle A in FIG. 3.

As mentioned above, the heel plate 32 extends between the foot plate 28 and the leg plate 30, and has a generally arcuate shape that forms a recess 46 that accommodates the heel 34 of the patient without placing localized pressure thereon. The heel plate 32 is shown best in the side view of FIG. 3 as a semi-circle having a preferred radius of approximately 3 inches. The heel plate 32 forms approximately a 45° angle between the proximal end 36 of the foot plate 28 and a similar 45° angle with the proximal end 42 of the leg plate 30 as shown in FIG. 4. Of course, the heel plate 32 may also have any shape (e.g., rectangular) known in the art for accommodating the heel 34 in a low or non pressurized position during the surgical procedure. The heel plate 32 is also narrower than the distal ends 38, 44 and is devoid of side walls or other flaring. The generally flat cross-section of the heel plate 32 is shown by the cross-section C-C in FIG. 2C relative to the more channeled cross-section of the distal end 38 of the foot plate 28 (represented by cross-section B-B in FIG. 2C) and the more semi-circular cross-section of the distal end 44 of the leg plate 30 (represented by the cross-section D-D in FIG. 2C). As such, the heel plate 32 permits visual inspection and palpation of the ankle area, which is important in certain surgical procedures (e.g., TKA). Importantly, the lower extremity support 16 supports the foot 12 and the lower leg 14 in a neutral position. This results in a more even distribution of forces exerted on the foot 12 and lower leg 14, such as those from TKA procedures (e.g., impacting knee replacement parts into the tibia bone). As such, the lower extremity support 16 prevents hyperextension of the ankle and toes of the patient.

FIG. 4 more specifically illustrates the ball mount 18 extending downwardly from the heel plate 32. The ball mount 18, as mentioned above, is configured for selective insertion into one of the plurality of apertures 20 in the base plate 22. More specifically, the ball mount 18 includes a connecting shaft 48 coupled underneath the recess 46 of the heel plate 32 by any suitable method known in the art (e.g., welding, mechanical fasteners, adhesive, integrally, etc.). The other end of the connecting shaft 48 is coupled to a reduced diameter extension shaft 49 that terminates into connection with an enlarged spherical protrusion or ball 50 affixed thereto for insertion into one of the apertures 20. As shown best in FIG. 4, the ball 50 has a diameter relatively larger than the extension shaft 49, but is relatively smaller than the connecting shaft 48. In one embodiment, the connecting shaft 48 may have a 1.5 inch diameter, the extension shaft 49 may have a 0.63 inch diameter and the ball 50 may have a 1 inch diameter. This relative sizing allows for positional adjustment of the lower extremity support 16 when mounted in one of the apertures 20, as discussed in more detail below. In the embodiment shown in FIG. 4, the connecting shaft 48 tapers into the reduced diameter of the connecting shaft 48, thereby creating a shoulder 52 that rests against a top surface 54 of the base plate 22. In this respect, the shoulder 52 facilitates easier insertion and removal into and out from the apertures 20. Moreover, the relatively narrower diameter extension shaft 49 permits greater motion of the ball 50 within the apertures 20, which facilitates the desired position of the tibia relative to the femur. The shafts 48, 49 are preferably cylindrical; although, the shafts 48, 49 may be any suitable shape known in the art (e.g., rectangular). Furthermore, the ball 50 may be any shape slidably receivable by the apertures 20 (e.g., also rectangular).

The base plate 22 provides a secure connection between the lower extremity support 16 and the operating table 26. As illustrated in FIGS. 5-9, the base plate 22 has a generally flat bottom surface 56 that securely sits on or otherwise mates with the top surface of the operating table 26. The top surface 54 of the base plate 22, as briefly mentioned above, provides a flat surface for the shoulder 52 to rest against when the ball 50 is inserted through one of the conical apertures 20. In the embodiments disclosed herein, the base plate 22 is relatively longer than it is wide to provide more positioning options regarding flexion of the knee 15. The base plate 22 is also preferably relatively flat so as to provide minimal surface interference on the operating table 26. Although, a person of ordinary skill in the art will readily recognize that the base plate 22 may vary in size, including its length, width and height. The base plate 22 could also be any shape known in the art (including, but not limited to, square, rectangular, circular, star-shaped, etc.). Preferably, the edges of the base plate 22 include chamfers or fillets 64 to round out the edges and reduce the risk of injury during handling by surgical personnel.

Figure 8:
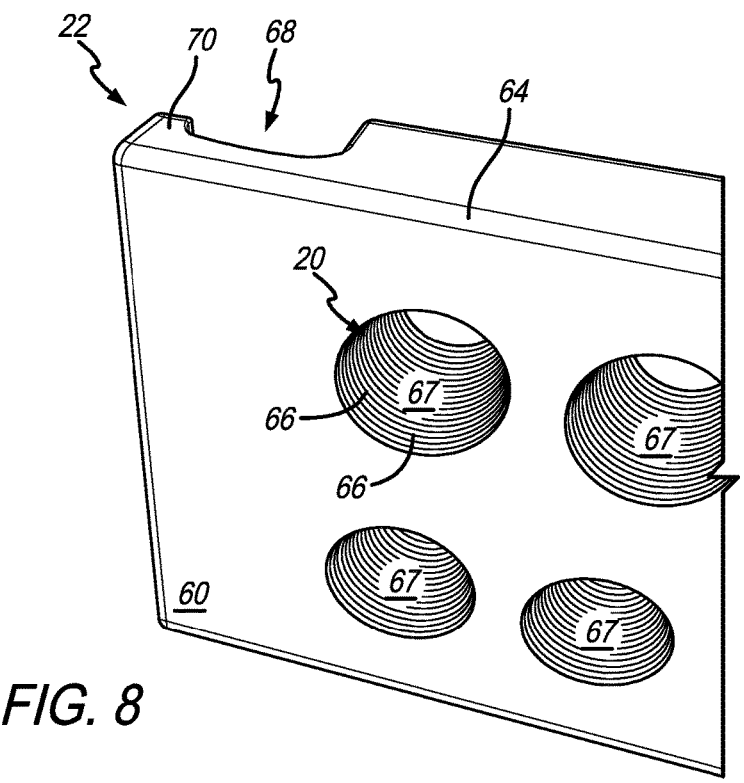
FIG. 8 is an enlarged perspective view of the bottom of the base plate, further illustrating a plurality of circumferential grooves formed within the conical apertures.
Figure 9:
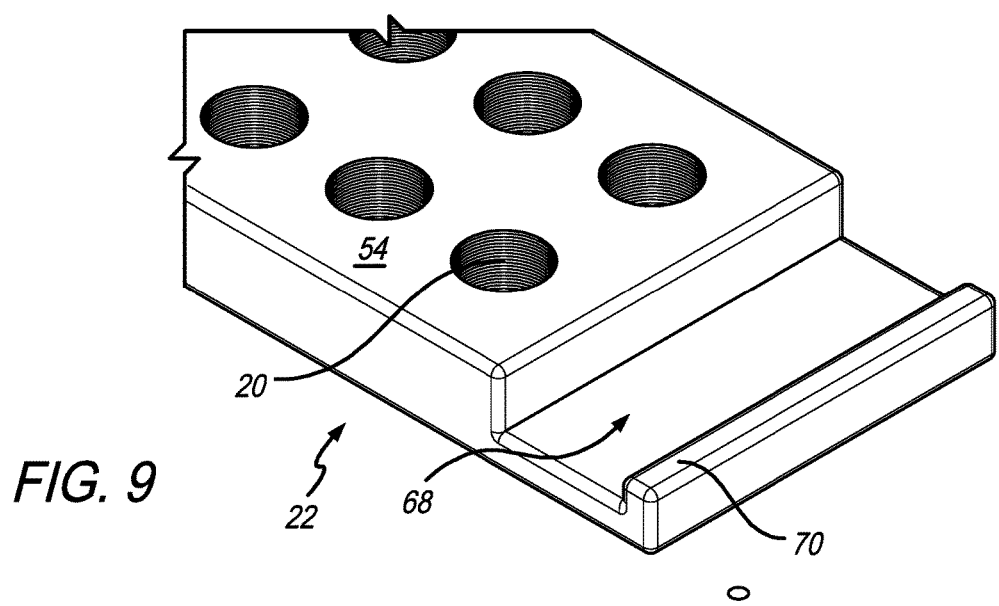
FIG. 9 is an enlarged perspective view of the base plate of FIG. 5, further illustrating an offset strip formed posterior to one of the channels in the base plate.

As mentioned above, the base plate 22 includes the plurality of apertures 20 having a size and shape for selectively receiving the ball mount 18, thereby positioning and supporting the lower extremity support 16. More particularly, the apertures 20 preferably extend through the width of the base plate 22, i.e., between the top surface 54 and the bottom surface 56. Additionally, the apertures 20 are conically shaped, and generally taper from a wider opening at the bottom surface 56 to a relatively smaller opening at the top surface 54, as best illustrated in FIG. 7B. The ball 50 of the mount 18 is sized for insertion through the relatively narrower opening at the top surface 54. In this respect, the tapered shoulder 52 sits on the top surface 54 and allows the extension shaft 49 and the ball 50 to project downwardly into the conical aperture 20. The inverse conical nature of the apertures 20 generally restricts movement closer to the top surface 54, while permitting relatively more movement toward the bottom surface 56. This configuration results in stabilization of the ball within the conical aperture with tangential or normal forces due to the angled wall. In this respect, the conical aperture 20 is preferably sized slightly wider than the ball 50 to permit selected slide-in reception thereof, while still horizontally confining the same. In one embodiment, for example, the apertures 20 may be approximately 50% wider at the bottom surface 56 than at the top surface 54. [Para 51] Additionally, one or more concentric grooves 66 may be bored into the interior surface 67 of the apertures 20. The grooves 66 disrupt the otherwise smooth interior surface 67, thereby providing friction resistance to outward sliding movement of the ball 50 out from within the conical aperture 20. As a result, the interior walls 67 of the apertures 20 may have a textured appearance (i.e., the interior wall 67 appears wavy along its vertical axis) as best shown in FIG. 8. The amount of friction within the apertures 20 may vary depending on the size (e.g., width, depth), shape and quantity of the grooves 66 formed in the interior surface 67. Preferably, the apertures 20 include at least one groove 66, but the apertures 20 may not have any of the grooves 66. In this embodiment, the interior surface 67 may be smooth.

The plurality of apertures 20 should be arranged on the base plate 22 to permit the lower extremity support 16, and consequently the knee 15, to be oriented in any position necessary or desirable for TKA and other knee surgeries. In the embodiment shown in FIGS. 5 and 7A, the base plate 22 includes a matrix of two columns having five evenly spaced apart apertures 20, for a total of ten apertures 20. The base plate 22 may include more or less of the apertures 20, and the apertures 20 may be arranged in any suitable manner (e.g., arranged in a series of concentric circles, star-shaped, etc.). The apertures 20 may also be cylindrical (i.e., the width at the top surface 54 is the same as the width at the bottom surface 56), rectangular (e.g., slot-like) or any other suitable shape (e.g., other polygonal shapes). Furthermore, the plurality of apertures 20 may extend through only a portion of the thickness of the base plate 22. The use of polygonal passageways, however, may permit only minimal rotation of the ball 50 therein. Alternately, the ball mount 18 may be rotatably attached to the lower extremity support 16.

As illustrated in FIGS. 5-7 and 9, the base plate 22 further includes at least one upwardly open channel 68 for receiving the foot rest 24, such as the KneeGrip® surgical positioning system manufactured and sold by SunMedica, Inc. of 1661 Zachi Way, Redding, Calif. 96003. More specifically, in the preferred embodiment, the base plate 22 includes two of the channels 68 at opposite ends of the base plate 22 as shown in FIGS. 6, 7A and 7B. Each channel 68 is essentially a cut-out (e.g., 60%-70% of the thickness of the base plate 22) from the top surface 54 of the base plate 22 and is formed with a respective elongated offset strip 70 on the outside of the base plate 22. As shown best in FIG. 7B, the offset strip 70 is at a height relatively lower than the top surface 54 to facilitate slide-in engagement with the KneeGrip® surgical positioning system or the like. The KneeGrip® surgical positioning system in particular is able to stabilize the base plate 22 on the sterile operating table 26 without any direct electrical contact therewith. Furthermore, as shown in FIG. 12, the reduced height of the offset strip 70 relative to the remainder of the base plate 22 allows the foot rest 24 to more fully engage with the channel 68. That is, the channel 68 can receive a larger portion of the foot rest 24 because one side of the channel 68 is partially open (i.e., the side with the offset strip 70). Preferably, the base plate 22 is symmetric and includes two of the upwardly open channels 68 disposed at opposite ends thereof. Additionally, the base plate 22 may include more or less (e.g., none) of the upwardly open channels 68, and the channels 68 may be disposed on any side of thereof. The aforementioned geometric relationships may vary depending on the specific needs of the application.

The components of the adjustable surgical support system 10 (e.g., the lower extremity support 16, the base support 22, etc.) are preferably constructed from aluminum (e.g., 6061 aluminum) and are able to withstand exposure to high heat (e.g., in an autoclave) or chemical cleaning products when undergoing sterilization sufficient for use and reuse in an operating room environment. Bar/plate stock and rod stock aluminum may be used instead of casting to reduce manufacturing cost. Aluminum also has the added advantage of being lightweight (e.g., relative to ferric alloys), thereby permitting easier transportation to and placement on the operating table 26. Although, other materials suitable for use with the adjustable surgical support system 10 disclosed herein may include, but are not necessarily limited to, stainless steel, sterilizable polymers such as reinforced polymers, plastic, etc.

Figure 10:
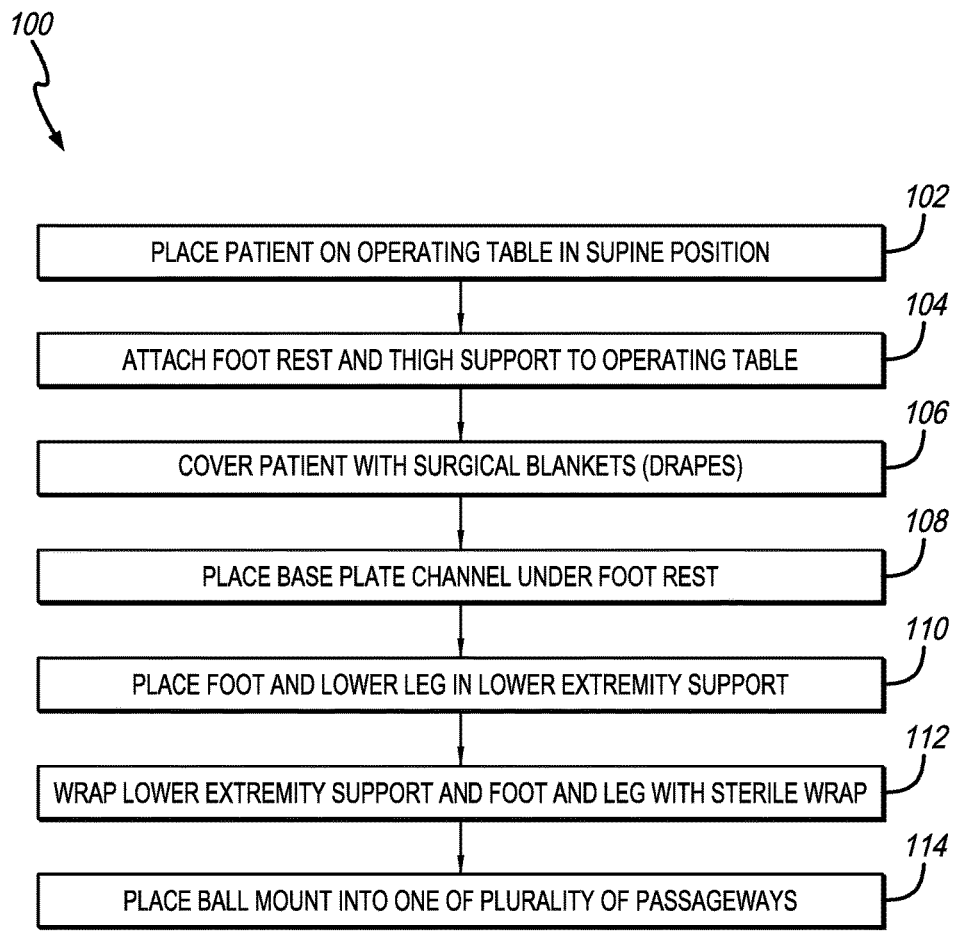
FIG. 10 is a flow chart illustrating a method for using the adjustable surgical support system in accordance with the embodiments disclosed herein.
Figure 11:
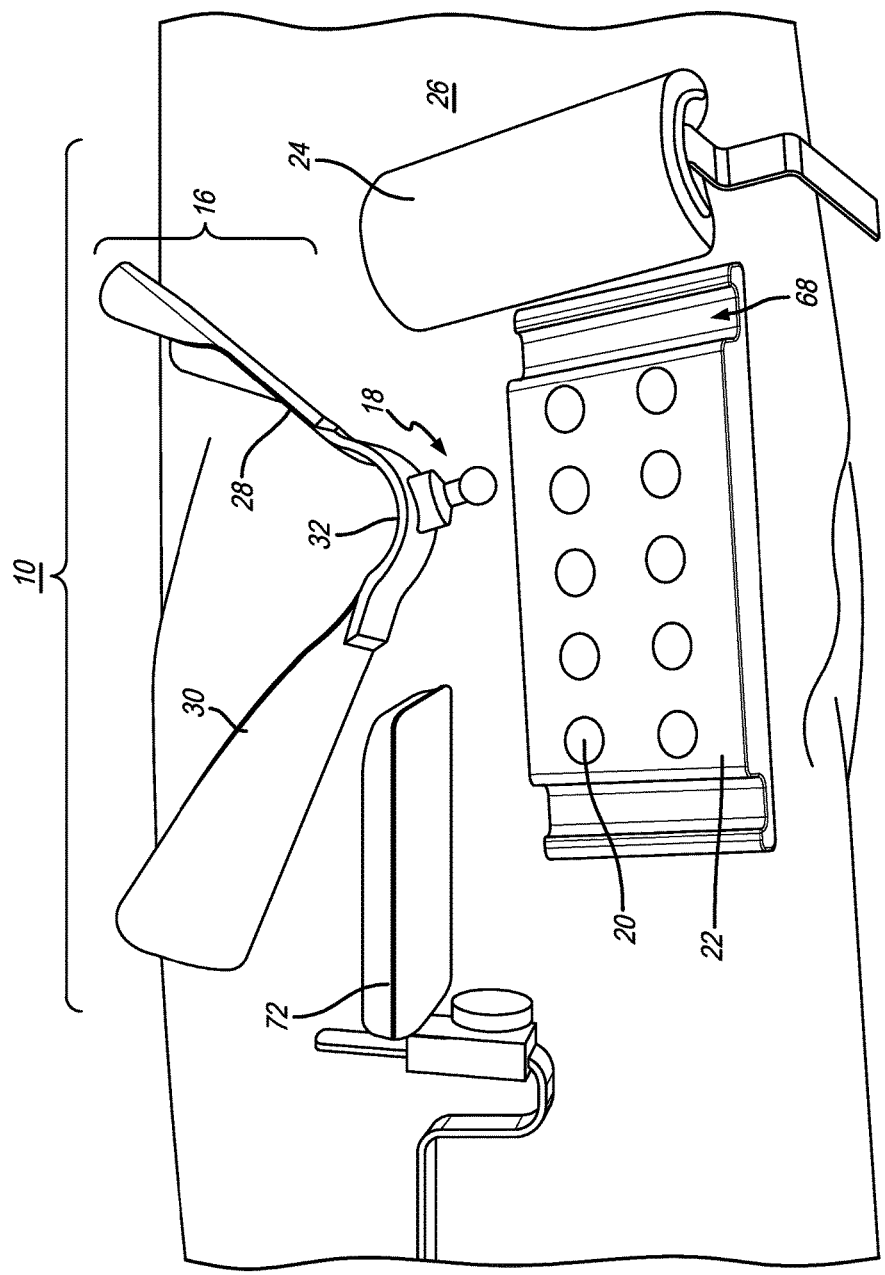
FIG. 11 is a perspective view generally illustrating the adjustable surgical support system components, for use with the methods disclosed herein.

FIG. 10 illustrates one method (100) for using the adjustable surgical support system 10 in accordance with the embodiments disclosed herein, the components of which are generally illustrated on an operating table 26 in FIG. 11. In this respect, the first step (102) is to place the patient on the operating table 26 in a supine position. The next step (104) is to attach the foot rest 24 and a lateral or thigh support 72 to the operating table 26 using, for example, the methods discussed in detail in U.S. Pat. No. 5,390,383 and/or U.S. Publication No. 2014/0059773, the contents of which are herein incorporated by reference in their entireties. The foot rest 24 should be positioned so the knee 15 of the patient is bent (e.g., at a 90°-100° angle). At this point, the angle between the lower leg 14 and a thigh 74 of the patient should be greater than the angle required by the upcoming surgical procedure, to accommodate the base plate 22. The thigh support 72 should hold the thigh 74 in a generally upright position, thereby preventing hip abduction and keeping the knee 15 in the proper lateral position. Surgical technicians may then cover the patient with any required surgical blankets 75 (FIGS. 13-15) in step (106).

As illustrated in FIG. 12, the next step (108) is to position one of the foot rests 24 over the offset strip 70 and into one of the channels 68. Here, the foot rest 24 can hold the base plate 22 in place without requiring connection to or contact with any of the metallic components of the operating table 26. More specifically, the lateral sidewalls of the channel 68 prevent the base plate 22 from moving under the foot rest 24. For example, the side wall of the channel 68 proximate to the offset strip 70 combined with the weight of the patient's foot 12 and the lower leg 14 prevent the base plate 22 from sliding toward the patient and away from foot rest 24. Preferably, a towel 76 is placed under the base plate 22 to further resist sliding movement of the base plate 22 on the surgical blankets (drapes). In this configuration, the base plate 22 is electrically insulated from the ground (i.e., the metal base of the operating table 26) by at least the padding on the foot rest 24, the surgical blankets 75 (drapes), and the towel 76 thereunder. As a result, electricity cannot readily conduct through the device and the patient because the device is not grounded. Advantageously, any potential electrical discharges from surgical procedures or equipment should not burn or otherwise injure the patient. At this point, the surgical technicians may finish preparing the patient for surgery by, e.g., wrapping the foot 12 and the lower leg 14 with a sterile wrap (e.g., Coban™ self-adherent wrap). FIG. 13 illustrates the adjustable surgical support system 10 after completion of step (108).

The next step (110) is to place the foot 12 in the lower extremity support 16. As illustrated in FIG. 14, the bottom of the foot 12 rests against the foot plate 28 such that the distal end 38 supports the toes and the side walls 40 prevent the foot 12 from sliding off the foot plate 28 or otherwise moving side-to-side. The heel plate 32 supports the heel 34, while permitting access thereto for visual inspection and palpation. The leg plate 30 cradles and supports the lower leg 14. This step (110) may optionally include placing a sterile foam pad 78 between the lower extremity support 16 and the foot 12 and/or the lower leg 14 to cushion the same. The next step (112) is to wrap the lower extremity support 16, the foot 12 and the lower leg 14 with a sterile wrap, such as the Coban™ self-adherent wrap, to prevent movement of the foot 12 and/or the lower leg 14 within the lower extremity support 16 during surgery.

Figure 16:
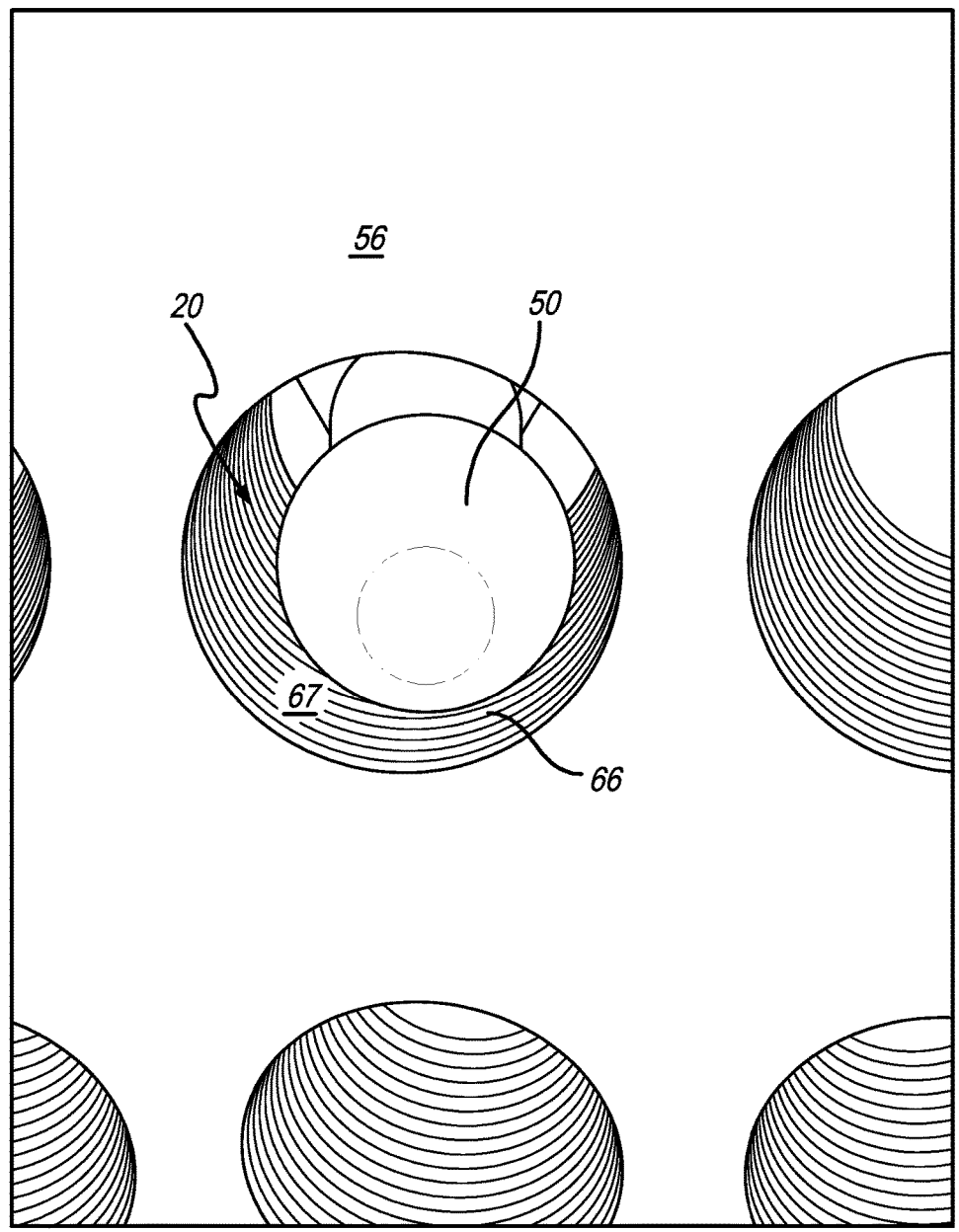
FIG. 16 is a bottom view of the base plate, illustrating floating engagement of the ball mount of the lower extremity support with one of the conical apertures in the base plate.

In step (114), the ball mount 18 is placed into one of the plurality of apertures 20 formed from the base plate 22, as illustrated in FIG. 15. As mentioned above and illustrated in FIG. 16, the apertures 20 horizontally confine the ball mount 18. The weight of the foot 12 and the lower leg 14 combined with the soft tissue tension in the knee stabilize the ball mount 18 by pushing the ball 50 against the side walls of the apertures 20. The ball 50 may still rotate within the apertures 20, thereby allowing the surgeon to vary the angle of the connecting shaft 48, and consequently varying the lower extremity support 16 relative to the base plate 22. The wider conical opening toward the bottom surface 56 of the aperture 20 provides additional space for the ball 50 to rotate. The angle of the wall 67 and the spherical nature of the ball mount 18 results in the lower extremity support 16 being stabilized by horizontal forces therein, such as would be encountered during knee surgery. This space between the ball 50 and the interior surface 67 of the aperture 20 is best shown in FIG. 16. As such, the position of the foot 12 and/or the lower leg 14 may be slightly adjusted as is necessary or desired during a specified surgical procedure. This, in turn, permits easy and efficient adjustment of the flexion and lateral/medial positioning of the knee 15. For example, movement of the ball 50 within one of the plurality of apertures 20 permits rotation of the tibia relative to the femur, thereby minimizing the tension and stress in the tissues connecting the knee joint.

Moreover, the position of the foot 12 and/or the lower leg 14 may be adjusted to a much greater extent by placing the ball mount 18 into a different one of the plurality of apertures 20. In this respect, changing the aperture 20 that receives the ball mount 18 acts as a course positional adjustment, whereas rotating the ball 50 within a specific one of the plurality of apertures 20 acts as a fine positional adjustment. This is particularly desirable in TKA procedures, where the surgeon typically moves the knee to different angles of flexion to view different parts thereof to achieve optimal fit and function of the prosthesis.

Although several embodiments have been described in detail for purposes of illustration, various modifications may be made without departing from the scope and spirit of the invention. Accordingly, the invention is not to be limited, except as by the appended claims.

What is claimed is:

1. An adjustable surgical support system, comprising:
a base plate having a plurality of retention apertures formed therein;
a lower extremity support having a heel plate positioned between a foot plate and a leg plate, the lower extremity support configured to receive and retain a portion of a lower extremity of a human body; and
a ball mount outwardly extending from the heel plate and selectively insertable in rotatable relation in and among the plurality of retention apertures such that the lower extremity support is selectively removable from one of the plurality of retention apertures and selectively insertable within another of the plurality of retention apertures to vary knee flexion and to vary a lateral or a medial position of a patient foot relative to a patient hip during surgery;
wherein the ball mount includes a connecting shaft having a diameter relatively larger than each of the plurality of retention apertures and the connecting shaft tapers into a shoulder terminating in a constant diameter extension shaft having a diameter relatively smaller than the connecting shaft, the shoulder comprising a width relatively larger than the plurality of retention apertures and contacting a top surface of the base plate in sliding relation relative thereto when the ball mount is selectively positioned within one of the plurality of retention apertures.

2. The support system of claim 1, wherein the heel plate includes a downwardly extending arcuate recess terminating below the foot plate and the leg plate such that a patient heel is supported by the foot plate and the leg plate in an elevated position above the arcuate recess.

3. The support system of claim 2, wherein the arcuate recess comprises a 2-4 inch radius.

4. The support system of claim 1, wherein the extension shaft terminates in a relatively larger diameter spherical mount insertable within any of the plurality of retention apertures.

5. The support system of claim 4, wherein the connecting shaft comprises a 1.0 to 2.0 inch diameter, the extension shaft comprises a 0.3 to 0.9 inch diameter, and the spherical mount comprises a 0.75 to 1.25 inch diameter.

6. The support system of claim 1, wherein each of the plurality of retention apertures comprises an inverse conical shape expanding downwardly from a top surface of the base plate.

7. The support system of claim 6, wherein the ball mount comprises a size and shape to contact an interior surface sidewall of the inverse conical retention aperture to apply a tangential force there-against when inserted therein.

8. The support system of claim 6, wherein the interior surface sidewall of each of the inverse conical retention apertures includes a plurality of concentric grooves for friction engagement with the ball mount when inserted therein.

9. The support system of claim 1, wherein the base plate includes at least one channel having a size and shape to selectively receive a clamp therein and an offset strip upwardly extending from one side of the at least one channel and having a height relatively smaller than a height of the base plate where the retention apertures are formed therein.

10. The support system of claim 9, wherein the clamp secures the base plate to an operating table in electrical isolation relative thereto.

11. An adjustable surgical support system, comprising:
a base plate having a plurality of retention apertures formed therein;
a lower extremity support configured to receive and retain a portion of a lower extremity of a patient, comprising a heel plate positioned between a foot plate and a leg plate, the heel plate including a downwardly extending arcuate recess terminating below the foot plate and the leg plate such that a patient heel is supported by the foot plate and the leg plate in an elevated position above the arcuate recess; and
a ball mount outwardly extending from the heel plate and including a connecting shaft that tapers into a shoulder having a width relatively larger than each of the plurality of retention apertures and contacts a top surface of the base plate in sliding relation relative thereto when a relatively smaller diameter spherical mount extending therefrom is selectively positioned within one of the plurality of retention apertures, the spherical mount being selectively insertable in rotatable relation in and among the plurality of retention apertures such that the lower extremity support is selectively removable from one of the plurality of retention apertures and selectively insertable within another of the plurality of retention apertures to vary knee flexion and to vary a lateral or a medial position of a patient foot relative to a patient hip during surgery.

12. The support system of claim 11, wherein the arcuate recess comprises a 2-4 inch radius and the spherical mount is selectively insertable in each of the plurality of retention apertures in 360 degree rotatable relation relative thereto.

13. The support system of claim 11, including an extension shaft positioned between the shoulder and the spherical mount, the connecting shaft comprising a 1.0 to 2.0 inch diameter, the extension shaft comprising a 0.3 to 0.9 inch diameter, and the spherical mount comprising a 0.75 to 1.25 inch diameter.

14. The support system of claim 11, wherein each of the plurality of retention apertures comprises an inverse conical shape expanding downwardly from a top surface of the base plate, the spherical mount having a size and shape to contact an interior surface sidewall of the inverse conical retention aperture having a plurality of concentric grooves formed therein to apply a tangential force there-against.

15. The support system of claim 11, wherein the base plate includes at least one channel having a size and shape to selectively receive a clamp therein and an offset strip upwardly extending from one side thereof adjacent the at least one channel, the offset strip having a height relatively smaller than the top surface of the base plate, wherein the clamp secures the base plate to an operating table in electrical isolation relative thereto.

16. An adjustable surgical support system, comprising:
a base plate having a plurality of retention apertures having an inverse conical shape expanding downwardly from a top surface of the base plate;
at least one channel formed in the base plate having a size and shape to selectively receive a clamp therein;
an offset strip upwardly extending from one side of the at least one channel and having a height relatively smaller than a height of the top surface of the base plate, wherein the clamp selectively engages the at least one channel over the offset strip to secure the base plate to an operating table in electrical isolation relative thereto;
a lower extremity support having a heel plate positioned between a foot plate and a leg plate, the lower extremity support configured to receive and retain a portion of a lower extremity of the human body; and
a ball mount outwardly extending from the heel plate and selectively insertable in rotatable relation in and among the plurality of retention apertures such that the lower extremity support is selectively removable from one of the plurality of retention apertures and selectively insertable within another of the plurality of retention apertures to vary knee flexion and to vary a lateral or a medial position of a patient foot relative to a patient hip during surgery.

17. The support system of claim 16, wherein the heel plate includes a downwardly extending arcuate recess terminating below the foot plate and the leg plate such that a patient heel is supported by the foot plate and the leg plate in an elevated position above the arcuate recess, and wherein the ball mount includes a connecting shaft having a diameter relatively larger than each of the plurality of retention apertures.

18. The support system of claim 17, wherein the arcuate recess comprises a 2-4 inch radius and the connecting shaft tapers into a shoulder terminating in a constant diameter extension shaft having a diameter relatively smaller than the connecting shaft.

19. The support system of claim 18, wherein the extension shaft terminates in a relatively larger diameter spherical mount insertable within any of the plurality of retention apertures, the connecting shaft comprises a 1.0 to 2.0 inch diameter, the extension shaft comprises a 0.3 to 0.9 inch diameter, and the spherical mount comprises a 0.75 to 1.25 inch diameter.

20. The support system of claim 18, wherein the shoulder comprises a width relatively larger than the plurality of retention apertures and contacts the top surface of the base plate in sliding relation relative thereto when the ball mount is selectively positioned within one of the plurality of retention apertures.

21. The support system of claim 16, wherein the ball mount comprises a size and shape to contact an interior surface sidewall of the inverse conical retention aperture to apply a tangential force there-against when inserted therein, the interior surface sidewall of each of the inverse conical retention apertures including a plurality of concentric grooves for friction engagement with the ball mount.

22. A method for securing and adjusting a lower extremity of a patient during surgery, comprising the steps of:
clamping a base plate having a plurality of retention apertures therein to an operating table in non-conductive relation relative thereto by securing a foot rest within a channel in the base plate and over an offset strip having a height relatively shorter than the height of the base plate, the channel preventing the base plate from moving under the foot rest;
securing the lower extremity of the patient to a lower extremity support comprising a heel plate positioned between a foot plate and a leg plate, the heel plate including a downwardly extending arcuate recess terminating below the foot plate and the leg plate such that a patient heel is supported by the foot plate and the leg plate in an elevated position above the arcuate recess;
inserting a ball mount outwardly extending from the heel plate into one of the retention apertures in the base plate;
removing and reinserting the ball mount in another of the retention apertures during surgery; and
rotating the ball mount within one of the retention apertures, wherein removing, reinserting, and rotating the ball mount varies knee flexion and a lateral or a medial position of a patient foot relative to a patient hip during surgery.

23. The method of claim 22, including the step of wrapping the combined lower extremity support and the lower extremity of the patient with a sterile wrap.

24. The method of claim 22, wherein the inserting or the reinserting step includes the step of positioning the ball mount within one of the retention apertures comprising an inverse conical shape.

25. The method of claim 24, including the step of tilting the ball mount within the retention aperture to tangentially contact a sidewall of the inverse conical retention aperture.

26. The method of claim 22, wherein the inserting step includes the step of placing a tapering shoulder having a width relatively larger than each of the plurality of retention apertures on a top surface of the base plate in sliding rotation relative thereto.

27. The method of claim 22, wherein the inserting step includes the step of course positional adjustment and the rotating step includes the step of fine positional adjustment.

28. An adjustable surgical support system, comprising:
a base plate having a plurality of retention apertures formed therein and comprising an inverse conical shape expanding downwardly from a top surface of the base plate;
a lower extremity support having a heel plate positioned between a foot plate and a leg plate, the lower extremity support configured to receive and retain a portion of a lower extremity of the human body; and
a ball mount outwardly extending from the heel plate and selectively insertable in rotatable relation in and among the plurality of retention apertures such that the lower extremity support is selectively removable from one of the plurality of retention apertures and selectively insertable within another of the plurality of retention apertures to vary knee flexion and to vary a lateral or a medial position of a patient foot relative to a patient hip during surgery, wherein an interior surface sidewall of each of the inverse conical retention apertures includes a plurality of concentric grooves for friction engagement with the ball mount when inserted therein.

29. The support system of claim 28, wherein the heel plate includes a downwardly extending arcuate recess terminating below the foot plate and the leg plate such that a patient heel is supported by the foot plate and the leg plate in an elevated position above the arcuate recess.

30. The support system of claim 29, wherein the arcuate recess comprises a 2-4 inch radius.

31. The support system of claim 28, wherein the ball mount includes a connecting shaft having a diameter relatively larger than each of the plurality of retention apertures.

32. The support system of claim 31, wherein the connecting shaft tapers into a shoulder terminating in a constant diameter extension shaft having a diameter relatively smaller than the connecting shaft.

33. The support system of claim 32, wherein the extension shaft terminates in a relatively larger diameter spherical mount insertable within any of the plurality of retention apertures.

34. The support system of claim 33, wherein the connecting shaft comprises a 1.0 to 2.0 inch diameter, the extension shaft comprises a 0.3 to 0.9 inch diameter, and the spherical mount comprises a 0.75 to 1.25 inch diameter.

35. The support system of claim 28, wherein the ball mount comprises a size and shape to contact an interior surface sidewall of the inverse conical retention aperture to apply a tangential force there-against when inserted therein.

36. The support system of claim 28, wherein the base plate includes at least one channel having a size and shape to selectively receive a clamp therein and an offset strip upwardly extending from one side of the at least one channel and having a height relatively smaller than a height of the base plate where the retention apertures are formed therein.

37. The support system of claim 36, wherein the clamp secures the base plate to an operating table in electrical isolation relative thereto.

38. An adjustable surgical support system, comprising:
a base plate having a plurality of retention apertures formed therein, the base plate including at least one channel having a size and shape to selectively receive a clamp therein;
an offset strip upwardly extending from one side of the at least one channel and having a height relatively smaller than a height of the base plate where the retention apertures are formed therein;
a lower extremity support having a heel plate positioned between a foot plate and a leg plate, the lower extremity support configured to receive and retain a portion of a lower extremity of the human body; and
a ball mount outwardly extending from the heel plate and selectively insertable in rotatable relation in and among the plurality of retention apertures such that the lower extremity support is selectively removable from one of the plurality of retention apertures and selectively insertable within another of the plurality of retention apertures to vary knee flexion and to vary a lateral or a medial position of a patient foot relative to a patient hip during surgery.

39. The support system of claim 38, wherein the heel plate includes a downwardly extending arcuate recess terminating below the foot plate and the leg plate such that a patient heel is supported by the foot plate and the leg plate in an elevated position above the arcuate recess.

40. The support system of claim 39, wherein the arcuate recess comprises a 2-4 inch radius.

41. The support system of claim 38, wherein the ball mount includes a connecting shaft having a diameter relatively larger than each of the plurality of retention apertures.

42. The support system of claim 41, wherein the connecting shaft tapers into a shoulder terminating in a constant diameter extension shaft having a diameter relatively smaller than the connecting shaft.

43. The support system of claim 42, wherein the extension shaft terminates in a relatively larger diameter spherical mount insertable within any of the plurality of retention apertures.

44. The support system of claim 43, wherein the connecting shaft comprises a 1.0 to 2.0 inch diameter, the extension shaft comprises a 0.3 to 0.9inch diameter, and the spherical mount comprises a 0.75 to 1.25 inch diameter.

45. The support system of claim 38, wherein each of the plurality of retention apertures comprises an inverse conical shape expanding downwardly from a top surface of the base plate.

46. The support system of claim 45, wherein the ball mount comprises a size and shape to contact an interior surface sidewall of the inverse conical retention aperture to apply a tangential force there-against when inserted therein.

47. The support system of claim 38, wherein the clamp secures the base plate to an operating table in electrical isolation relative thereto.

48. A method for securing and adjusting a lower extremity of a patient during surgery, comprising the steps of:
clamping a base plate having a plurality of retention apertures therein to an operating table in non-conductive relation relative thereto;
securing the lower extremity of the patient to a lower extremity support comprising a heel plate positioned between a foot plate and a leg plate, the heel plate including a downwardly extending arcuate recess terminating below the foot plate and the leg plate such that a patient heel is supported by the foot plate and the leg plate in an elevated position above the arcuate recess;
inserting a ball mount outwardly extending from the heel plate into one of the retention apertures in the base plate;
removing and reinserting the ball mount in another of the retention apertures during surgery, wherein the inserting or the reinserting step includes the step of positioning the ball mount within one of the retention apertures comprising an inverse conical shape;
tilting the ball mount within the retention aperture to tangentially contact a sidewall of the retention aperture having the inverse conical shape; and
rotating the ball mount within one of the retention apertures, wherein removing, reinserting, and rotating the ball mount varies knee flexion and a lateral or a medial position of a patient foot relative to a patient hip during surgery.

49. The method of claim 48, including the step of wrapping the combined lower extremity support and the lower extremity of the patient with a sterile wrap.

50. The method of claim 48, wherein the inserting step includes the step of placing a tapering shoulder having a width relatively larger than each of the plurality of retention apertures on a top surface of the base plate in sliding rotation relative thereto.

51. The method of claim 48, wherein the inserting step includes the step of course positional adjustment and the rotating step includes the step of fine positional adjustment.

52. A method for securing and adjusting a lower extremity of a patient during surgery, comprising the steps of:
clamping a base plate having a plurality of retention apertures therein to an operating table in non-conductive relation relative thereto;
securing the lower extremity of the patient to a lower extremity support comprising a heel plate positioned between a foot plate and a leg plate, the heel plate including a downwardly extending arcuate recess terminating below the foot plate and the leg plate such that a patient heel is supported by the foot plate and the leg plate in an elevated position above the arcuate recess;
inserting a ball mount outwardly extending from the heel plate into one of the retention apertures in the base plate;
placing a tapering shoulder having a width relatively larger than each of the plurality of retention apertures on a top surface of the base plate in sliding rotation relative thereto;
removing and reinserting the ball mount in another of the retention apertures during surgery; and
rotating the ball mount within one of the retention apertures, wherein removing, reinserting, and rotating the ball mount varies knee flexion and a lateral or a medial position of a patient foot relative to a patient hip during surgery.

53. The method of claim 52, including the step of wrapping the combined lower extremity support and the lower extremity of the patient with a sterile wrap.

54. The method of claim 52, wherein the inserting or the reinserting step includes the step of positioning the ball mount within one of the retention apertures comprising an inverse conical shape.

55. The method of claim 52, wherein the inserting step includes the step of course positional adjustment and the rotating step includes the step of fine positional adjustment.

* * * * *